United States Patent
Mainardi et al.

(10) Patent No.: US 12,106,841 B2
(45) Date of Patent: Oct. 1, 2024

(54) SYSTEM AND METHODS FOR CALCULATING, DISPLAYING, MODIFYING, AND USING SINGLE DIETARY INTAKE SCORE REFLECTIVE OF OPTIMAL QUANTITY AND QUALITY OF CONSUMABLES

(71) Applicant: SOCIETE DES PRODUITS NESTLE S.A., Vevey (CH)

(72) Inventors: Fabio Mainardi, Bursins (CH); Hilary Green, Chatillens (CH)

(73) Assignee: Societe des Produits Nestle S.A., Vevey (CH)

( * ) Notice: Subject to any disclaimer, the term of this patent is extended or adjusted under 35 U.S.C. 154(b) by 70 days.

(21) Appl. No.: 16/624,150

(22) PCT Filed: Jun. 12, 2018

(86) PCT No.: PCT/EP2018/065418
§ 371 (c)(1),
(2) Date: Dec. 18, 2019

(87) PCT Pub. No.: WO2018/234083
PCT Pub. Date: Dec. 27, 2018

(65) Prior Publication Data
US 2020/0227156 A1    Jul. 16, 2020

Related U.S. Application Data

(60) Provisional application No. 62/523,908, filed on Jun. 23, 2017.

(51) Int. Cl.
G16H 20/60        (2018.01)

(52) U.S. Cl.
CPC .................. G16H 20/60 (2018.01)

(58) Field of Classification Search
CPC ................................................... G16H 20/60
(Continued)

(56) References Cited

U.S. PATENT DOCUMENTS

| 11,037,669 | B2 * | 6/2021 | Solari | ............... G16H 50/30 |
| 2003/0232067 | A1 | 12/2003 | Wolf | |
| 2013/0108993 | A1 | 5/2013 | Katz | |

FOREIGN PATENT DOCUMENTS

| JP | 2013058085 A | 3/2013 |
| WO | 2015001595 A1 | 1/2015 |

(Continued)

OTHER PUBLICATIONS

Adam Drewnowski, "Concept of a nutritious food: toward a nutrient density score", Am J Clin Nutr 2005;82:721-32 (Year: 2005).*

(Continued)

*Primary Examiner* — Joshua B Blanchette
(74) *Attorney, Agent, or Firm* — K&L Gates LLP

(57) ABSTRACT

Embodiments of the disclosed system calculate a single score ("SDIS") for dietary intake over a period of time. In one embodiment, the single score is an indication of whether a subset of measurable nutrients (determined to be indicative of nutritional health) and energy consumed are within a healthy range that is specific to a user. Embodiments of the disclosed system determine whether each nutrient consumed falls within a healthy range. This range may be calculated by, for example, using a plurality of possible minimum intake values and an upper limit (if one exists) for each nutrient. Similarly, the system determines whether the energy consumed falls within a healthy range. The averaged nutrient score is then multiplied by an energy score to arrive at the final score. In an embodiment, the system particularly emphasizes the impact of the energy score treated as a multiplier rather than as a nutrient.

19 Claims, 12 Drawing Sheets

| | 1310 | 1312 | 1314 |
|---|---|---|---|
| | Outstanding | 0.8-1.0 | Your diet provides the right amounts of energy and key nutrients required for good health |
| | Good | 0.6-0.8 | Your diet is much better than the average in your population, but there is still room for improvement |
| | Average | 0.4-0.6 | Your diet is similar or a little better than the average in your population, but falls short of recommendations |
| | Poor | 0.2-0.4 | Your diet is similar or below the average in your population, and in need of improvement |
| | Very poor | < 0.2 | Your diet is well below the average in your population, and in need of a lot of improvement |

(58) Field of Classification Search
USPC .......................................................... 705/2, 3
See application file for complete search history.

(56) References Cited

FOREIGN PATENT DOCUMENTS

| WO | 2016050958 | 4/2016 | | |
|----|------------|--------|---|---|
| WO | WO-2016050958 A1 | * | 4/2016 | ............. G16H 20/60 |

OTHER PUBLICATIONS

Wikipedia, "Speech Recognition", Jun. 4, 2014 (Year: 2014).*
Drewnowski, Adam "Concept of a nutritious food: toward a nutrient density score1-3" Am J Clin Nutr, 2005, vol. 82, pp. 721-732.
Zhang et al., "Nutrient Profile - A New Index for Food Nutrition Evaluation", Acta Nutrimenta Sinica, vol. 31, Issue No. 01, Feb. 28, 2009, 11 pages (6 pages of English Translation and 5 pages of Official copy).
Zhu et al., "Selection of Basis of Calculation for Nutrient Profile", Nutrition Newsletter, vol. 01, Feb. 15, 2014, 12 pages (6 pages of English Translation and 6 pages of Official copy).
Scarborough et al., "Testing Nutrient Profile Models using Data from a survey of Nutrition Professionals", Public Health Nutrition, vol. 10, Issue No. 04, Apr. 1, 2007, pp. 337-345, XP093128714.
Rayner et al., "Nutrient Profiles: Options for Definitions for use in relation to Food Promotion and Children's diets", Final Report, British Heart Foundation Health Promotion Research Group, Oct. 1, 2004, pp. 1-196, XP093128726.
"Nutri-Score", Wikipedia, Retrieved from <URL: https://en.wikipedia.org/wiki/Nutri-Score>, Feb. 7, 2024, pp. 1-11, XP093128699.
Office Action received for Application No. 201880036415.0, mailed on Jan. 20, 2023, 13 Pages (10 pages of Official copy and 3 pages of English Translation).
European Office Action for Appl No. 18 731 791.2-1126 dated Feb. 15, 2024.

* cited by examiner

| Sodium | | | 1272.26 mg | 2300 | 100 |
|---|---|---|---|---|---|
| Potassium | | 4700 | 2883.38 mg | 5710 | 61 |
| Food Folate | | 400 | 202.66 μg | 673 | 51 |
| Vit D | | 15 | 2.52 μg | 26 | 17 |

FIG. 9

|  | 1212 | | | 1214 | | | 1216 | | |
|---|---|---|---|---|---|---|---|---|---|
| 1210 | Mediterranean | Vegetarian | US-style | Mediterranean | Vegetarian | US-style | Mediterranean | Vegetarian | US-style |
| Energy | 1802 | 1826 | 1797 | 1998 | 2028 | 2003 | 2203 | 2230 | 2198 |
| Added sugars | 1 | 1 | 1 | 1 | 1 | 1 | 1 | 1 | 1 |
| Calcium | 0.97 | 1 | 1 | 1 | 1 | 1 | 1 | 1 | 1 |
| Carbohydrate | 1 | 1 | 1 | 1 | 1 | 1 | 1 | 1 | 1 |
| Saturated fat | 1 | 1 | 1 | 1 | 1 | 1 | 1 | 1 | 1 |
| Total fat | 1 | 1 | 1 | 1 | 1 | 1 | 1 | 1 | 1 |
| Food Folate | 1 | 0.99 | 1 | 1 | 0.92 | 1 | 0.94 | 0.63 | 0.96 |
| Fiber | 1 | 1 | 1 | 1 | 1 | 1 | 1 | 0.76 | 1 |
| Iron | 0.87 | 1 | 0.73 | 0.87 | 1 | 0.87 | 1 | 1 | 1 |
| Magnesium | 1 | 1 | 1 | 1 | 1 | 1 | 1 | 1 | 1 |
| Potassium | 0.46 | 0.45 | 0.45 | 0.53 | 0.53 | 0.52 | 0.65 | 0.63 | 0.64 |
| Protein | 1 | 1 | 1 | 1 | 1 | 1 | 1 | 1 | 1 |
| Sodium | 1 | 1 | 1 | 1 | 1 | 1 | 1 | 1 | 1 |
| Vitamin A | 1 | 1 | 1 | 1 | 1 | 1 | 1 | 1 | 1 |
| Vitamin C | 1 | 1 | 1 | 1 | 1 | 1 | 1 | 1 | 1 |
| Vitamin D | 0.29 | 0.25 | 0.34 | 0.3 | 0.25 | 0.35 | 0.33 | 0.26 | 0.37 |
| Vitamin E | 0.45 | 0.5 | 0.41 | 0.55 | 0.6 | 0.52 | 0.65 | 0.7 | 0.62 |
| Total score | 0.88 | 0.89 | 0.87 | 0.89 | 0.89 | 0.89 | 0.91 | 0.87 | 0.91 |

FIG. 12

| High HEI (95) 1928 kcals | | Low HEI (15) 2029 kcals | |
|---|---|---|---|
| name | Grams | name | grams |
| Water, tap [nhanes] - 94000100 | 1422 | Doughnut, cake type [nhanes] - 53520110 | 208 |
| Millet, puffed [nhanes] - 57307500 | 6.56 | | |
| Milk, soy, ready-to-drink, not baby's [nhanes] - 11320000 | 321.56 | Coffee, made from ground, regular [nhanes] - 92101000 | 518 |
| Blueberries, raw [nhanes] - 63203010 | 74 | Cream, half and half [nhanes] - 12120100 | 121 |
| Wheat germ, plain [nhanes] - 57412000 | 28.25 | | |
| Flax seeds [nhanes] - 43104000 | 42 | | |
| Papaya, raw [nhanes] - 63133010 | 210 | | |
| Egg, whole, boiled or poached [nhanes] - 31103010 | 44 | Sugar, white, granulated or lump [nhanes] - 91101010 | 12.5 |
| Rice, brown, cooked, fat added in cooking, made with oil [nhanes] - 56205012 | 171.5 | Tea, herbal, presweetened with sugar [nhanes] - 92306020 | 592 |
| Beans, lima, immature, cooked, from frozen, fat not added in cooking [nhanes] - 75204012 | 180 | Cheeseburger with tomato and/or catsup, on bun [nhanes] - 27510310 | 114 |
| Cherries, sweet, raw (Queen Anne, Bing) [nhanes] - 63115010 | 229.6 | | |
| Avocado, raw [nhanes] - 63105010 | 100.5 | Frankfurter or hot dog sandwich, beef, plain, on white bread [nhanes] - 27564070 | 170 |
| Vinegar [nhanes] - 64401000 | 5 | | |
| Rice, brown, cooked, fat added in cooking, made with oil [nhanes] - 56205012 | 171.5 | Tomato catsup [nhanes] - 74401010 | 2.5 |
| Olive oil [nhanes] - 82104000 | 9 | Water, tap [nhanes] - 94000100 | 237 |
| Stewed chickpeas, Puerto Rican style [nhanes] - 41310150 | 260 | | |

FIG. 14

SYSTEM AND METHODS FOR CALCULATING, DISPLAYING, MODIFYING, AND USING SINGLE DIETARY INTAKE SCORE REFLECTIVE OF OPTIMAL QUANTITY AND QUALITY OF CONSUMABLES

CROSS REFERENCE TO RELATED APPLICATIONS

The present application is a National Stage of International Application No. PCT/EP2018/065418, filed on Jun. 12, 2018, which claims priority to U.S. Provisional Patent Application No. 62/523,908, filed on Jun. 23, 2017, the entire contents of which are being incorporated herein by reference.

COPYRIGHT NOTICE

A portion of the disclosure of this patent document contains material that is subject to copyright protection. The copyright owner has no objection to the photocopy reproduction of the patent document or the patent disclosure in exactly the form it appears in the Patent and Trademark Office patent file or records, but otherwise reserves all copyright rights whatsoever.

TECHNICAL FIELD

The present disclosure relates in general to systems and methods for calculating the impact of dietary intake on the health of individuals or populations. More specifically, the present disclosure relates to systems and methods for determining a single optimal score that reflects both the optimal "quality" (i.e., the nutrient density of food to be consumed) and "quantity" (i.e., the amount of food/energy to consume to give a maximum nutritional benefit) of consumed items. Such systems and methods permit the calculation of a single score for quality and quantity to more accurately reflect a person's optimal energy (calorie) intake and beneficially offer a new approach for evaluating, tracking, and optimizing dietary intake for individuals and populations.

BACKGROUND

Over the past century, essential nutrient deficiencies have decreased, especially in the developed countries, and infectious disease rates have dropped. At the same time, the rates of chronic, diet-related diseases have risen. National surveys (e.g., the National Health and Nutrition Examination Survey in the US) reveal poor quality eating patterns. Cardiovascular disease, high blood pressure, type 2 diabetes, some cancers, and poor bone health have been shown to have some degree of correlation with such eating patterns. The proportion of overweight or obese people is alarmingly increasing. It is important to realize that these poor eating patterns correspond to excessive consumption of certain nutrients, like saturated fat or sugar, but also to the low intake of other important nutrients, like vitamin B6, potassium, or folate.

Making healthier food choices can help prevent non-communicable diseases such as obesity, cardiovascular disease, diabetes and some cancers. Food-based dietary guidelines, like the *Dietary Guidelines for Americans*, provide general population recommendations for healthful eating. Such guidelines can drive content for nutrition labels, health claims, nutrition education, menu planning, as well as marketing and advertising on food products. Recommendations for healthier food choices are generally promulgated in two levels of granularity: at the level of food groups (e.g., eat more fruits, eat more whole grains) or at the nutrient level. However, these generalized guidelines are not designed to provide personalized nutrition recommendations at the macro- or micronutrient level.

In addition to nutrient profiling models for foods, there are models designed to assess the nutritional quality of meals or diets. These tend to be based on nutrient adequacy and reduced risk of diet-related non-communicable diseases (Fransen and Ocké 2008), and in this way reflect national and/or international dietary guidelines. A notable example is the US Healthy Eating Index which was originally developed over 20 years ago by the USDA (Kennedy et al 1995). This has more recently been updated and a new version (HEI 2015) can be used to assess compliance with the 2010 Dietary Guidelines for Americans (Guenther et al). Other countries have used a similar model to assess adherence to their own dietary guidelines, including Canada (Garriguet 2009), Brazil (Andrade et al 2013), Spain (Norte Navarro and Moncada (2011) and Australia (Roy et al 2016). These indices use thresholds and healthy ranges of both foods and nutrients, as recommended by the dietary guidelines in the respective countries. Consequently, the higher the score, the closer a diet follows or conforms to the recommendations of the dietary guidelines. These HEI tools are dynamic, in the sense that they are updated when the dietary guidelines change. This allows them to measure adherence to the current dietary guidelines, but makes them less useful for longitudinal comparisons of dietary quality within a given population.

Another profiling model that can be applied to whole diets is Nestle's Nutrient Balance Concept (NBC), which was developed using the USDA Food Composition Database (SR 27). This provides scores for the relative content of key nutrients that should be promoted or discouraged in foods, meals and whole diets (Fern et al 2015). Like the Healthy Eating Index, the NBC uncouples diet quality from diet quantity. In all cases, the scores represent diet quality for a given level of energy intake, but do not properly reflect the (potentially negative) impact on health of either over- or under-consumption of energy.

Substantial efforts have been made to quantify and track the impact of particular consumables, such as ingredients, foods, meals, or diets, on the overall health of individuals. For example, every five years since 1980, the United States Department of Agriculture (USDA) along with the Department of Health and Human Services (HHS) releases so-called Dietary Guidelines for Americans. The USDA states that these Guidelines provide advice about consuming fewer calories, making informed food choices, and being physically active to attain and maintain a healthy weight. (http://www.cnpp.usda.gov/DietaryGuidelines).

Likewise, many other national and international agencies have published recommendations for daily intake of nutrients, for apparently healthy individuals of all ages. These recommendations are applied in many contexts, including: composition of diets for schools, prisons, hospitals or nursing homes: development of new food products in the industry; decision making by health-care policy makers and public health officials.

To this end, the Institute of Medicine (TOM) in the US has created a general framework called the Dietary Reference Intakes (DRI); this reference framework has been subsequently adopted by other countries. Under the IOM's framework, for a given nutrient for which adequate knowledge is available, a set of DRI is defined as follows:

Estimated Average Requirement (EAR): the average daily nutrient intake level estimated to meet the requirement of half the healthy individuals in a particular life stage and gender group Recommended Dietary Allowance (RDA): the average daily nutrient intake level sufficient to meet the nutrient requirement of nearly all (e.g., 97 to 98 percent) healthy individuals in a particular life stage and gender group. The RDA may be expressed or represented as a percentage, as well as a quantity (i.e., grams).

Tolerable Upper Level (UL): the highest average daily nutrient intake level likely to pose no risk of adverse health effects to nearly all individuals in the general population; as intake increases above the UL, the potential risk of adverse effects increases Adequate Intake (AI): a recommended average daily nutrient intake level based on observed or experimentally determined approximations or estimates of nutrient intake by a group (or groups) of apparently healthy people that are assumed to be adequate; it is used when an RDA cannot be determined While the DRIs discussed above provide a general framework into which individuals can seek to fit themselves, they are nonetheless inadequate tools to enable individuals to track the actual impact of consumables on overall health. Specifically, because these mechanisms are nothing more than guidelines, it is difficult for individuals to determine the actual goals they should be attempting to achieve, and whether/when those goals have been achieved. That is, it is difficult for individuals to assess the quality and quantity of their meals or diets, over a period of time, rather than specific foods.

The DRIs discussed above, as defined by the IOM, define a very wide range of acceptable food intake for many nutrients, for some nutrients these ranges have an infinite length because the upper limit of intake is undefined. Therefore, the representations presented by the DRIs are not always reflective of overconsumption.

While certain known tools may enable users to assess the quality of food, such known tools do not provide the ability to measure dietary intake in relation to both quality and quantity of food consumption.

To assist nutrition professionals and individuals in navigating more specific nutrition intake goals, food scientists have attempted to develop scoring systems to rate the healthfulness or unhealthfulness of foods. However, reviewers have noted these systems are often methodologically weak. In certain existing schemes that attempt to apply scores to foods, a single score is determined and applied to the food itself without consideration of the individual consuming the food or the amount of the food consumed. This is ineffective, as the health of a given food depends both on the individual consuming the food (e.g., the caloric or other nutritional needs of the individual) and the amount of the food consumed (e.g., a half-cup of ice cream versus a half-gallon of ice cream).

Another important difference with measures like the Healthy Eating Index or the Nutrients Rich Food Index is that the measures are density measures only, meaning that the limits used to score dietary components are defined with respect to caloric intakes (e.g., per 1000 kilo-calories). This means that the score is independent of the actual amounts consumed (multiplying all the amounts by the same factor does not change the value of the index). However, the dietary reference intakes for micro-nutrients are defined as absolute amounts, and such definitions are not directly related to the energy intake. It would be beneficial for a system and method that calculates scores reflecting not only the quality (i.e., the nutrient content) of a consumable but also the quantity (i.e., the amount of energy or calories) of the consumable consumed.

Known systems and schemes are also deficient because they are not constructed at an appropriate level of granularity to improve scoring for heterogeneous populations or individuals. Instead, one set of values is used to define a single score for populations and all individuals. This lack of granularity prohibits known systems and schemes from being customized to different individual users with different individual nutritional needs.

What is needed is a system that uses a combination of the quality and quantity of nutrients consumed over a period of time, including the energy requirement adapted to an individual, to develop a score for an individual's food intake over that period of time.

What is further needed is a system that calculates a healthy range for an individual over a period of time.

What is further needed is a system that calculates a customized score based on adjustable sets of nutrients and adjustable energy values to design score profiles for a particular use case or purpose, such as for performance in athletics.

What is still further needed is a system that can calculate scores to be applied at the level of a population, to detect deficiencies, deviations from healthy eating patterns, and more generally to detect any pattern at the population level or historical trends.

The present disclosure describes a nutritional intake scoring system that satisfies the needs described above. Moreover, the present disclosure reflects algorithms and methodologies that have been fully validated based on both ideal and real data. Thus, the present disclosure describes a system and methods that overcome the shortcomings of prior nutritional management techniques described above.

SUMMARY

Most nutrient profiling models are designed to assess the quality of foods, rather than meals or diets, and those that do tend to uncouple quality from quantity. One of the primary objectives of the embodiments of the system and methods disclosed herein is to determine a single dietary intake score ("SDIS") reflective of both nutritional quality and quantity of an amount of consumed food over a period of time.

The instant disclosure is based, in various embodiments, on the premise of first creating an SDIS derived from the weighted average of nutrients and multiplied by energy. In stark contrast to other schemes known to the inventor, the instant disclosure beneficially incorporates the energy consumption into the overall score (the SDIS) by multiplying the nutrient average by an energy score, giving energy a vital role in this profiling model. In various embodiments, the score calculated by the disclosed methodology can be interpreted as a utility function and techniques from economic analysis and game theory can then be applied to the context of nutrition and dietary planning. Accordingly, it is believed that the system and methods disclosed herein can be used as a valid and reliable indicator of how balanced and adequate a diet is with respect to an individual's particular nutritional needs, including particular caloric intake needs.

In various embodiments, the system and methods disclosed herein create an SDIS using knowledge and distributional properties of the DRI or other intake recommendation regimes for a chosen list of nutrients (preferably a subset of nutrients determined to be of critical importance) and an energy goal/requirement adapted for an individual or population. In an embodiment, the SDIS has a maximal score obtained when energy intake and all the relevant nutrients are within the healthy range for a given individual during a time period. In an embodiment, consumption below or above this range will result in a lower score, with energy consumption below or above the range having a proportionate impact on lowering the score.

Various embodiments of the disclosed system are based on the premise that all nutrients have healthy ranges for consumption. That is, embodiments of the disclosed system are based on the premise that there are no healthy or unhealthy nutrients, and hence no intrinsically healthy or unhealthy foods. Instead, for each nutrient (and thus for each food), a person consumes an amount that is either inside or outside a healthy range for consumption. In these embodiments, the healthy ranges of nutrients and energy can be different for different individuals, meaning that an assessment of health depends on the needs of a specific individual. For example, the healthy ranges of particular nutrients or energy can vary for different people depending on whether a person is pregnant or lactating, whether a person has diabetes, whether a person is obese, whether a person is a critical care patient, whether a person has allergies, or whether a person is an athlete. As described below, by varying the healthy range for different nutrients in a way that is customized to the person, and combining it with a customized energy intake for each person, the calculated SDIS provided by the disclosed system is also customized to each individual user, and provides a more accurate reflection of a healthy score.

In some embodiments, the disclosed system and method takes into account a healthy range, with an "upper" and "lower" limit of the healthy range as appropriate for particular nutrients. Whenever intake of a particular nutrient is within the healthy range, the score for that nutrient is at a maximum. In particular, embodiments of the system disclosed herein use the RDA (or AI score when the RDA is not available) to determine the lower limit of the healthy range. A reasonable upper limit is selected in the context of a healthy eating pattern of a given energy level in accordance with dietary guidelines. The disclosed system can then determine a personalized, minimum intake amount and a maximum intake amount ("healthy range") of a nutrient for an individual over a given period of time. These scores are aggregated and multiplied by an energy score in order to calculate the SDIS, with the SDIS accurately reflecting the import of energy intake to overall nutritional health.

In various embodiments, the system disclosed herein calculates SDIS tailored to an individual based on the individual's caloric intake range and corresponding healthy ranges of nutrient intakes for a given time period. The calculated scores are based on whether nutrient intake falls within a healthy range, and are affected not only by under-consumption of nutrients but also by over-consumption of nutrients. These scores enable individuals to determine whether they are consuming enough nutrients, and to the extent they are not, to determine which additional nutrients need to be consumed. In an embodiment, the lower limit, where a score of zero will be awarded for under consumption of a nutrient, is chosen with respect to a percentile of usual intake in a chosen population. In an embodiment, the upper limit, where a score of zero will be awarded for over consumption of a nutrient, is chosen with respect to amounts of nutrient contained in typical foods rich in that particular nutrient. In an alternative embodiment, the upper limit is chosen with respect to the UL.

In some embodiments, nutrients, or parameters, are chosen according to what one wants to measure, meaning that the set of nutrients selected for weighted average is a subset of all the nutrients found in a consumable. In some embodiments, energy itself is scored according to a similar function as nutrients, being calculated using the IOM. Once an energy score is obtained, energy is used as a factor in the overall SDIS by multiplying the average nutrient score by the energy score. This technique causes energy to assume an overarching role, which is reflective of its importance to the overall SDIS. In some embodiments, this energy score depends on several parameters: age, gender, height, weight, and physical activity level. In some embodiments, computationally, this score may be calculated very efficiently through a matrix computation. Further, because the upper limit of the healthy range is dependent upon energy, the SDIS is energy-adjusted not only by virtue of the multiplication of the weighted average by the energy factor discussed above, but also through the choice of healthy ranges.

It is important to note that the score calculated according to some embodiments of the system disclosed herein is not additive. In particular, adding a 'healthy' food to a healthy menu can potentially decrease the total score: this will happen if the energy or some nutrients exceed their upper limits. On the other hand, adding an 'unhealthy' food in small amount might in some cases improve the score. Therefore, quality and quantity are beneficially intertwined, and the SDIS does not account for them separately. Nutrient-dense foods are certainly an essential component of any healthful diet; however, there is enough flexibility to allow for small amounts of less nutrient-dense foods in the context of a healthy diet. This is in accordance with the Dietary Guidelines for Americans 2015-2020.

Embodiments of the disclosed system offer a variety of software and analytic tools to assess, plan, and optimize diets on a person-by-person (or population group-by-population group) basis, and take into account both recommended intake amounts and endpoints for minimum and maximum intake amounts.

Various embodiments of the disclosed system further advantageously provide nutritional advice to users based on calculated scores. For example, embodiments of the disclosed system determine amounts of nutrients that would be needed to place an individual in the healthy amount range for those nutrients. These embodiments then analyze a database of consumables (e.g., foods or ingredients) to determine combinations of consumables that will provide the needed amounts of nutrients to place the user in the healthy amount ranges while still remaining within the optimal caloric intake range for that individual.

Accordingly, it should be appreciated that various embodiments of the disclosed system advantageously enable the calculation of an SDIS for an individual by performing the following steps:
 (1) Storing indications of a plurality of nutrients (preferably a subset of all nutrients of a set of consumed foods) to be scored;
 (2) Storing indications of healthy ranges for each of the stored nutrients, including lower intake limits determined by combining various recommendations from various appropriate organizations in a way specific to an individual;

(3) Storing indications of endpoints for nutrient consumption to enable the system to adjust for over- and under-consumption beyond the endpoints, as is appropriate for each nutrient;

(4) Storing score weighting and individual tolerance values for each nutrient and/or individual;

(5) For a particular consumable, compute a nutrient score for each component nutrient;

(6) Compute the average nutrient score for the consumable by applying weight values for each nutrient;

(7) Compute the energy score; and (8) Multiply the energy score by the average nutrient score to obtain the final score or SDIS.

Further advantages of the instant disclosure will be apparent from the following detailed description and associated figures.

BRIEF DESCRIPTION OF THE FIGURES

FIG. 9 is an example graphical user interface display based on this disclosure.

FIG. 12 is an example chart based on this disclosure indicating nutrient scores and overall SDISs for different recommended consumption amounts.

FIG. 14 is a chart comparison of a high HEI diet with a low HEI diet.

DETAILED DESCRIPTION

Figure 1:
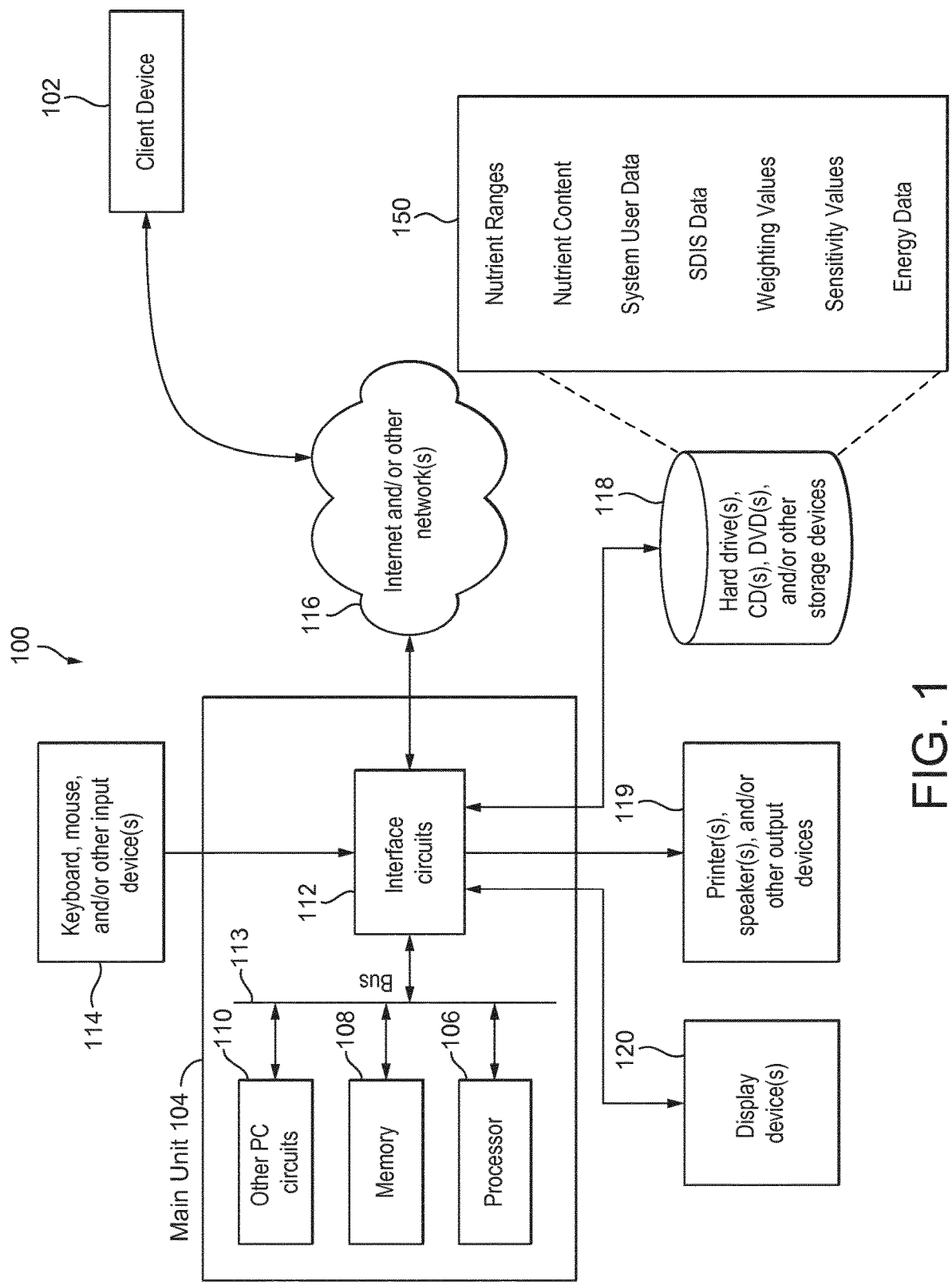
FIG. 1 is a block diagram of an example system according to one embodiment of the present disclosure.

In general, embodiments of the system disclosed herein calculate and display an SDIS indicating the impact of consumption of nutrients and energy. These scores are tailored to the particular individual consuming the consumable, such that the score reflects the impact of the consumption given the individual's specific needs. In addition, the score reflects whether or not endpoints have been exceeded, either by over- or under-consuming a consumable, with the score being adjusted as appropriate (e.g., more drastically modified) if consumption is not within the range defined by the endpoints. Importantly, embodiments of the disclosed system factor in energy consumption in a way that is reflective of the actual contribution of energy to the overall health of an individual than has been done in prior scoring systems.

Most nutrient profiling models are designed to assess the nutritional quality of foods, rather than meals or diets, and those that do tend to uncouple quality from quantity. Energy and key nutrients are used in this disclosure to provide a score for dietary quality and quantity. The disclosure is based on personalized energy and nutrient ranges for a time period (e.g., 24 hours). The main way that these ranges were defined was by using specified RDAs of key nutrients as well as the nutrient content of two exemplary healthy menu plans designed to meet US food-based dietary guidelines.

In general, the system disclosed herein calculates and displays an SDIS derived from the weighted average of a subset of nutrients as identified herein for a given period of time. In an embodiment, the subset is chosen for ease of tracking coupled with accuracy in reflecting the overall health through a diet. This average is then multiplied by the score for energy. The score for energy, for example, could be a number from 0 to 1. Another example could be a number from 0 to 100. Multiplying the weighted average of non-energy nutrients by the energy score creates a system where caloric intake outside a healthy caloric range is penalized. In an example of the present use of the model, all the nutrients are given an equal weight, but the model could be tailored to emphasize specific nutrients of interest. In addition, in the present use of the model the nutrition score is provided for a time period of 24 hours, but the model could be used to assess nutrition over any time period of interest.

An SDIS may be calculated, for example, based on a number of parameters: (1) a chosen list of nutrients; (2) an energy requirement, or energy goal, adapted to the individual, (3) a list of 4 numbers, for each nutrient, fitting the intake of that nutrient into a general healthy eating pattern, in conformity with the current dietary guidelines (for a given country); (4) a fixed period of time; and/or (5) a weight for each nutrient. The input, for example, could be provided in the form of a list of foods consumed, with their respective amounts. The output could be a single SDIS number, ranging from 0 to a maximum value (usually 100 or 1).

The 4 parameters mentioned in point 3 above define, for a given nutrient, a 'healthy range' and the tolerances for intakes outside the healthy range. The principle of the SDIS is that a maximal score is obtained when energy intake and all the relevant nutrients are within the healthy range for a given individual during a time period, for example, 24 hours. Consumption below, or above this healthy range will result in lower scores.

Various embodiments of the disclosed system satisfies the general goal, given a particular diet, to recommend a set of new amounts of the given foods, and eventually a set of new foods, in order to improve the overall nutritional content of the diet. Since the overall score depend on the general characteristics of the individual (gender, age, weight, body measurements, physical activity level, and other health-related conditions like pregnancy or lactation etc.), the recommendations to improve the overall score likewise depend on characteristics of the individual. The disclosed system and methods in certain embodiments recommend either reductions or additions to the baseline meal, and further look for nutrients whose intake is above the recommended upper limit and then it calculates the minimal quantity of each food to be removed from the meal in order to keep each nutrient below its upper limit. For the additions, the system queries a food database to determine which foods, if added to the meal, would increase the global score. In some embodiments, an increase in global score is accepted only if no single nutrient has its scored worsened by more than 1 point. A set of filters can be selected to avoid specific food groups, or specific search terms. Such filtering allows for more personalized dietary advice. These recommendations try to push the baseline meal as close as possible to the healthy range for every nutrient.

More particularly, in various embodiments, the system disclosed herein calculates and displays scores indicating the nutritional impact of consuming a consumable, such as a food, on the individual consuming the consumable. In these embodiments, the system determines and stores one or more indications of the needs of the individual for whom the scores are being calculated, such as by determining an optimal caloric intake range for an individual over a given period of time. In these embodiments, the system also determines and stores endpoints for the consumable, such that the system can appropriately handle situations where consumption is outside the range defined by the endpoints (e.g., over- or under-consumption). In certain embodiments, the disclosed system also determines and stores indications of such ranges of nutrients the individual should consume given the caloric intake range for a given period of time, such as by determining and storing a range of the amount of certain micronutrients (in mg) that the individual should consume in a day based on the caloric intake range for the day. The disclosed system then enables the user to indicate consumables (such as food items) that he or she has consumed or plans to consume. For each indicated food item, a database or datastore of the disclosed system stores an indication of the nutrient content per amount of that food item. The system uses the nutritional content information, multiplied by the amount of food item consumed over time, to determine the total nutritional intake over time for that particular food item.

In various embodiments, after determining the ranges of nutrients that are optimal for a particular individual at a particular caloric intake range in a particular time, and after knowing at least one consumed or to-be-consumed food item in that time period, the system calculates one or more nutrient scores for the individual. These nutrient scores indicate the nutritional impact of the indicated food item. In general, these scores are calculated by determining, for each nutrient tracked by the system, whether the nutrient content of the food item falls within the optimal or healthy range for that nutrient. In general, if an individual over- or under-consumes a nutrient, the disclosed system beneficially reflects that over- or under-consumption by more drastically affecting the score for that nutrient (and thus the overall single dietary intake score).

In one embodiment, a nutrient score is calculated for each nutrient contained in a food item. The system thereafter aggregates the nutrient scores using a weighting function to indicate the relative importance of each nutrient to the overall health of the individual's nutrition; the aggregate nutrient score is called the average nutrient score. In some such embodiments, the weighting function takes into account whether or not the individual has over- or under-consumed any individual nutrients; if the individual has, the disclosed system in some embodiments increases the impact of that nutrient on the average nutrient score to reflect the fact that over- or under-consumption can have a relatively drastic impact on an individual's overall nutritional health. Then, an energy score is calculated based on a recommended lower and upper energy intake for the individual. Then, the nutrient score is multiplied by the energy score leading to the SDIS. In an embodiment, the SDIS is calculated on a scale of 0 to 100, where scores closer to 100 indicate greater fulfilment of the nutritional needs of the individual over a particular time period. In an alternative embodiment, the score can be between 0 and 1.

As further described in detail below, various embodiments of the disclosed system also provide an advisory function, wherein the system suggests combinations of foods that will result in an improved or optimal SDIS. For example, if a user accesses the system after breakfast and indicates the foods he or she had for breakfast, the disclosed system may calculate an SDIS for the breakfast foods, but may also determine what nutrients would need to be consumed over the remainder of the day, as well as how much energy to consume over the remainder of the day, for the individual to consume nutrients and energy in the optimal ranges (and to generate an optimal SDIS) for that day. In this embodiment, the system uses these calculated nutrient amounts to determine combinations of food that can be consumed throughout the remainder of the day to ensure that the individual's nutritional goals are achieved as fully as possible while still consuming a number of calories within that individual's optimal caloric intake range. Thus, the system disclosed herein can operate not only as a tracking system, but also as a recommendation engine to recommend consumables to help individuals reach their nutritional goals.

In embodiments of the disclosed system, the SDIS described is calculated by determining a plurality of individual component nutrient scores, which are then aggregated into an average nutrient score and multiplied by an energy score. In various embodiments of the system and methods disclosed herein, an SDIS algorithm is used to calculate an SDIS based on a plurality of inputs, including:

List of consumed nutrients
Amount of consumed nutrients
Gender
Age
Body Mass
Special conditions (e.g., pregnancy, lactating, etc.)

The term "nutrient" is used repeatedly herein. In some embodiments, the term "nutrient" as used herein refers to compounds having a beneficial effect on the body e.g. to provide energy, growth or health. The term includes organic and inorganic compounds. As used herein the term nutrient may include, for example, macronutrients, micronutrients, essential nutrients, conditionally essential nutrients and phytonutrients. These terms are not necessarily mutually exclusive. For example, certain nutrients may be defined as either a macronutrient or a micronutrient depending on the particular classification system or list.

In various embodiments, the term "macronutrient" is used herein consistent with its well understood usage in the art, which generally encompasses nutrients required in large amounts for the normal growth and development of an organism. Macronutrients in these embodiments may include, but are not limited to, carbohydrates, fats, proteins, amino acids and water. Certain minerals may also be classified as macronutrients, such as calcium, chloride, or sodium.

In various embodiments, the term "micronutrient" is used herein consistent with its well understood usage in the art, which generally encompasses compounds having a beneficial effect on the body, e.g. to help provide energy, growth or health, but which are required in only minor or trace amounts. The term in such embodiments may include or encompass both organic and inorganic compounds, e.g. individual amino acids, nucleotides and fatty acids; vitamins, antioxidants, minerals, trace elements, e.g. iodine, and electrolytes, e.g. sodium, and salts thereof, including sodium chloride.

In one embodiment, the nutrients may be the major macronutrients of carbohydrates, proteins and fats from which the SDIS is calculated.

In another embodiment, the nutrients may be a combination of macronutrients and micronutrients from which the SDIS is calculated.

In a further embodiment, the combination of macronutrients and micronutrients from which the SDIS is calculated include one of a least carbohydrate, protein, total fat, fiber, calcium, potassium, magnesium, iron, food folate, vitamin A, vitamin C, vitamin D, vitamin E, sodium, saturated fat, and added sugars.

In another embodiment, the nutrients used to calculate the SDIS include all of carbohydrate, protein, total fat, fiber, calcium, potassium, magnesium, iron, food folate, vitamin A, vitamin C, vitamin D, vitamin E, sodium, saturated fat, and added sugars.

In yet another embodiment, the list of nutrients used to calculate the SDIS score may be used together with the dietary sources of these nutrients by food group such as vegetables, fruits, grains, dairy, protein foods, oils, the color of fruits and vegetables, and/or other factors.

In yet another embodiment, the list used to calculate the SDIS includes the nutrients that are found on the label of processed food packaging. In this embodiment, the label of the processed food packaging contains information relating to carbohydrate, protein and/or total fat content of the food.

It should be appreciated that "energy" is not treated as a nutrient; rather, it is a separate component of the overall SDIS that is incorporated with a nutrient score as described in detail below. The list of nutrients used by the SDIS, together with the main dietary sources of these nutrients, and the rationale for inclusion, is provided in the following table. Applicant has recognized that the Key Nutrients on US Food Labels, as listed below, may in certain embodiments be most likely to be of concern to consumers. In the below example, a US consumer may be most likely to be deficient in the Shortfall nutrients of Table 1, and more likely to have consumed an excess amount of nutrients as those listed in the column titled "Nutrients consumed in excess." This rationale may be updated to correspond to different countries and population groups, including consumers with specific health conditions.

TABLE 1

List of Nutrients and Food Group

| Food Group | Key Nutrients on US Food Label | Shortfall nutrients | Nutrients consumed in excess |
|---|---|---|---|
| Vegetables | dietary fiber, vitamin A, vitamin C, iron. | Dietary fiber, iron, potassium, vitamin C, vitamin E, magnesium, folate | |
| Fruit | dietary fiber, vitamin C. | Dietary fiber, potassium, Vitamin C | |
| Grains | dietary fiber, iron, vitamin A. | Dietary fiber, iron, magnesium, folate | |
| Dairy | calcium, vitamin A, protein. | Calcium, potassium, vitamin D (in fortified products), magnesium | |
| Protein foods | protein, iron | Vitamin D, vitamin E | |
| Oils | fat | Vitamin E | Sodium, saturated fat, sugars |
| Other | | | |

In another embodiment, one or more devices carried by the user could provide real-time information to the system when the user is in a food purchasing establishment such as a grocery store or a restaurant. Devices such as RFID readers, NFC readers, wearable camera devices, and mobile phones could receive or determine (such as by scanning RFID tags, reading bar codes, or determining the physical location of a user) foods that are available to a user at a particular grocery store or restaurant. The disclosed system could then make recommendations taking into account what foods could be immediately purchased or consumed by the user. In one such embodiment, when a user sits down at a restaurant, the disclosed system may push information to the user's mobile phone recommending that the user select certain items from the menu to optimize the user's SDIS for a given time period. In still other embodiments, a voice recognition feature recognizes inputs provided vocally by a user. In one such embodiment, the voice recognition system listens as a user orders at a restaurant; in other embodiments, the voice recognition system enables the user to speak directly the items he or she has consumed or will consume. In another embodiment, the disclosed system could use geolocation to provide appropriate exercise recommendations based on the user's location. For example, an app on a user's phone, tablet, or computer could provide the user (e.g., in a chat box) different activity tips if the user is at work, in a gym, or at home.

Nutrient Health Score Calculation

Referring now to FIG. 1, a block diagram is illustrated showing an example of the electrical systems of a host device 100 usable to implement at least portions of the computerized SDIS and recommendation system disclosed herein. In one embodiment, the device 100 illustrated in FIG. 1 corresponds to one or more servers and/or other computing devices that provide some or all of the following functions: (a) enabling access to the disclosed system by remote users of the system; (b) serving web page(s) that enable remote users to interface with the disclosed system; (c) storing and/or calculating underlying data, such as recommended caloric intake ranges, recommended nutrient consumption ranges, and nutrient content of foods, needed to implement the disclosed system; (d) calculating and displaying component or SDIS; and/or (e) making recommendations of foods or other consumables that can be consumed to help individuals reach an optimal SDIS.

In the example architecture illustrated in FIG. 1, the device 100 includes a main unit 104 which preferably includes one or more processors 106 electrically coupled by an address/data bus 113 to one or more memory devices 108, other computer circuitry 110, and/or one or more interface circuits 112. The one or more processors 106 may be any suitable processor, such as a microprocessor from the INTEL PENTIUM® or INTEL CELERON® family of microprocessors. PENTIUM® and CELERON® are trademarks registered to Intel Corporation and refer to commercially available microprocessors. It should be appreciated that in other embodiments, other commercially-available or specially-designed microprocessors may be used as processor 106. In one embodiment, processor 106 is a system on a chip ("SOC") designed specifically for use in the disclosed system.

In one embodiment, device 100 further includes memory 108. Memory 108 preferably includes volatile memory and non-volatile memory. Preferably, the memory 108 stores one or more software programs that interact with the hardware of the host device 100 and with the other devices in the system as described below. In addition or alternatively, the programs stored in memory 108 may interact with one or more client devices such as client device 102 (discussed in detail below) to provide those devices with access to media content stored on the device 100. The programs stored in memory 108 may be executed by the processor 106 in any suitable manner.

The interface circuit(s) 112 may be implemented using any suitable interface standard, such as an Ethernet interface and/or a Universal Serial Bus (USB) interface. One or more input devices 114 may be connected to the interface circuit 112 for entering data and commands into the main unit 104. For example, the input device 114 may be a keyboard, mouse, touch screen, track pad, track ball, isopoint, and/or a voice recognition system. In one embodiment, wherein the device 100 is designed to be operated or interacted with only via remote devices, the device 100 may not include input devices 114. In other embodiments, input devices 114 include one or more storage devices, such as one or more flash drives, hard disk drives, solid state drives, cloud storage, or other storage devices or solutions, which provide data input to the host device 100.

One or more storage devices 118 may also be connected to the main unit 104 via the interface circuit 112. For example, a hard drive, CD drive, DVD drive, flash drive, and/or other storage devices may be connected to the main unit 104. The storage devices 118 may store any type of data used by the device 100, including data regarding preferred nutrient ranges, data regarding nutrient contents of various food items, data regarding users of the system, data regarding previously-generated single dietary intake scores, data representing weighting values for calculating single dietary intake scores, sensitivity values for calculating nutrient scores, data regarding ideal energy intake, data regarding past energy consumption, and any other appropriate data needed to implement the disclosed system, as indicated by block 150. Alternatively or in addition, storage devices 118 may be implemented as cloud-based storage, such that access to the storage 118 occurs via an internet or other network connectivity circuit such as an Ethernet circuit 112.

One or more displays 120, and/or printers, speakers, or other output devices 119 may also be connected to the main unit 104 via the interface circuit 112. The display 120 may be a liquid crystal display (LCD), a suitable projector, or any other suitable type of display. The display 120 generates visual representations of various data and functions of the host device 100 during operation of the host device 100. For example, the display 120 may be used to display information about the database of preferred nutrient ranges, a database of nutrient contents of various food items, a database of users of the system, a database of previously-generated single dietary intake scores, and/or databases to enable an administrator at the device 100 to interact with the other databases described above.

In the illustrated embodiment, the users of the computerized SDIS and recommendation system interact with the device 100 using a suitable client device, such as client device 102. The client device 102 in various embodiments is any device that can access content provided or served by the host device 100. For example, the client device 102 may be any device that can run a suitable web browser to access a web-based interface to the host device 100. Alternatively or in addition, one or more applications or portions of applications that provide some of the functionality described herein may operate on the client device 102, in which case the client device 102 is required to interface with the host device 100 merely to access data stored in the host device 100, such as data regarding healthy nutrient ranges or nutrient content of various food items.

In one embodiment, this connection of devices (i.e., the device 100 and the client device 102) is facilitated by a network connection over the Internet and/or other networks, illustrated in FIG. 1 by cloud 116. The network connection may be any suitable network connection, such as an Ethernet connection, a digital subscriber line (DSL), a WiFi connection, a cellular data network connection, a telephone line-based connection, a connection over coaxial cable, or another suitable network connection.

In one embodiment, host device 100 is a device that provides cloud-based services, such as cloud-based authentication and access control, storage, streaming, and feedback provision. In this embodiment, the specific hardware details of host device 100 are not important to the implementer of the disclosed system-instead, in such an embodiment, the implementer of the disclosed system utilizes one or more Application Programmer Interfaces (APIs) to interact with host device 100 in a convenient way, such as to enter information about the user's demographics to help determine healthy nutritional ranges, to enter information about consumed foods, and other interactions described in more detail below.

Access to device 100 and/or client device 102 may be controlled by appropriate security software or security measures. An individual user's access can be defined by the device 100 and limited to certain data and/or actions, such as inputting consumed food or viewing calculated scores, according to the individual's identity. Other users of either host device 100 or client device 102 may be allowed to alter other data, such as weighting, sensitivity, or healthy range values, depending on those users' identities. Accordingly, users of the system may be required to register with the device 100 before accessing the content provided by the disclosed system.

In a preferred embodiment, each client device 102 has a similar structural or architectural makeup to that described above with respect to the device 100. That is, each client device 102 in one embodiment includes a display device, at least one input device, at least one memory device, at least one storage device, at least one processor, and at least one network interface device. It should be appreciated that by including such components, which are common to well-known desktop, laptop, or mobile computer systems (including smart phones, tablet computers, and the like), client device 102 facilitates interaction among and between each other by users of the respective systems.

In various embodiments, devices 100 and/or 102 as illustrated in FIG. 1 may in fact be implemented as a plurality of different devices. For example, the device 100 may in actuality be implemented as a plurality of server devices operating together to implement the media content access system described herein. In various embodiments, one or more additional devices, not shown in FIG. 1, interact with the device 100 to enable or facilitate access to the system disclosed herein. For example, in one embodiment the host device 100 communicates via network 116 with one or more public, private, or proprietary repositories of information, such as public, private, or proprietary repositories of nutritional information, nutrient content information, healthy range information, energy information, environmental impact information, or the like.

In one embodiment, the disclosed system does not include a client device 102. In this embodiment, the functionality described herein is provided on host device 100, and the user of the system interacts directly with host device 100 using input devices 114, display device 120, and output devices 119. In this embodiment, the host device 100 provides some or all of the functionality described herein as being user-facing functionality.

As noted above, the system disclosed herein is premised, in various embodiments, on the idea of promoting health through good nutrition. The notion of promoting health through good nutrition is built on the idea that all nutrients have healthy ranges for consumption. That is, the notion of good nutrition is built on the idea that there are no intrinsically healthy nutrients, and no intrinsically unhealthy nutrients. Instead, for any possible nutrient, consumption of that nutrient can be either inside of a healthy range or outside of a healthy range. While the healthy range can vary for different individuals, consumption of a nutrient inside the healthy range is generally viewed as being healthy consumption of that nutrient.

In various embodiments, the system disclosed herein is arranged as a plurality of modules, wherein each module performs a particular function or set of functions. The modules in these embodiments could be software modules executed by a general purpose processor, software modules executed by a special purpose processor, firmware modules executing on an appropriate, special-purpose hardware device, or hardware modules (such as application specific integrated circuits ("ASICs")) that perform the functions recited herein entirely with circuitry. In embodiments where specialized hardware is used to perform some or all of the functionality described herein, the disclosed system may use one or more registers or other data input pins to control settings or adjust the functionality of such specialized hardware. For example, a hardware module may be used that is programmed to analyze a nutrient score based on a piecewise continuous function that is increasing in a first segment, flat in a second segment, and decreasing in a third segment. In this example, the hardware may be programmed to evaluate the function, and one or more inputs to the hardware may be configured to receive inputs of, for example, the input value at which the first segment meets the second segment, the input value at which the second segment meets the third segment, and parameters to indicate the rate at which the third segment is decreasing (e.g., a slope or a function defining the shape of the third segment). In still other embodiments, where the modules to perform various functionality described herein are software modules executable by hardware, the modules may take the form of apps or subsets of apps that may be designed to run on a processor executing a particular, predefined operating system environment. In other embodiments, the function does not need to be an increasing function, but could take on any shape. For example, the function could be decreasing, curved, etc.

Figure 2:
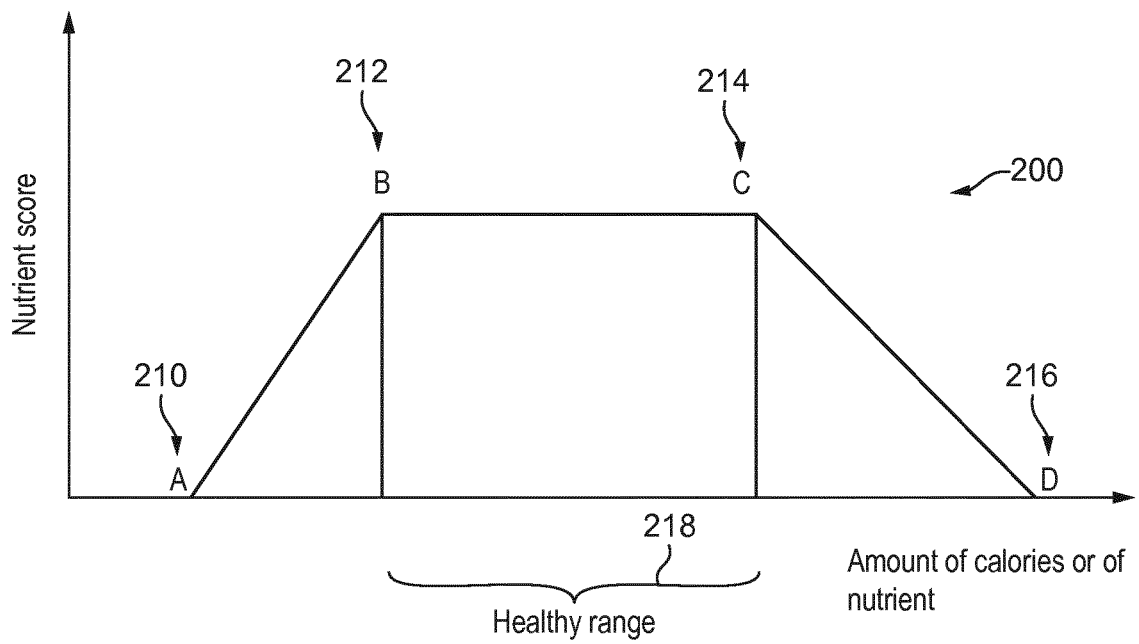
FIG. 2 is an example nutrient scoring graph for a nutrient that can be both over-consumed and under-consumed.

FIG. 2 discloses a scoring function 200 for each nutrient, defining a function for nutrients that have a healthy range, and over-consumption and under-consumption may be penalized with a score of 0. Points B (212) and C (214) define the healthy range (218), which is the ideal range for the intake of the nutrient (or calories). Whenever the intake is within the healthy range 218, the score for a particular nutrient is at a maximum. Point A (210) defines a score of 0, and a score of 0 is awarded when consumption of a nutrient is below the healthy range. Point A (210) is determined with respect to a tolerance for under-consumption of a nutrient. Point D (216) defines a score of 0 when consumption of a nutrient is above the healthy range. Point D (216) is determined with respect to a tolerance for over-consumption of a nutrient. Note that points A (210) and D (216) do not need to be symmetrical. FIG. 2 is defined by a function, with the properties of being: piecewise linear, continuous. This function is defined as S(x), where x is the amount of a nutrient, in its proper units of measurement. The function for FIG. 2 is:

$$S(x) = \begin{cases} 0 & \text{if } x \leq x_A \\ \frac{x - x_A}{x_B - x_A} & \text{if } x_A \leq x \leq x_B \\ 1 & \text{if } x_B \leq x \leq x_C \\ \frac{x_D - x}{x_D - x_C} & \text{if } x_C \leq x \leq x_D \\ 0 & \text{if } x \geq x_D \end{cases} \quad (1)$$

In various embodiments, "x" in Equation 1 above need not refer to nutrients. In particular, in some embodiments, "x" may represent an amount, or volume, of food from a particular food group (e.g., 3 servings of fruit or 3 cups of fruit), an amount of a particular kind of a food in a food group (e.g., 3 grams of dark green vegetables), an amount of a particular food product (e.g., 0.5 hamburgers), an amount of a vitamin supplement. In still other embodiments, "x" represents an amount of a different kind of consumable, such as a amount of consumed food from a "food category" as that concept is discussed elsewhere herein.

In this example, the maximum value of 1 has been chosen for simplicity. Given a list of k nutrients: $n_1, n_2, \ldots, n_k$, each of them will correspond to a function $S_i(x)$, all defined by this equation, equation (1), but with different values of A,B,C,D.

Given a list of total foods with quantities, an average nutrient score can be extracted with the total amounts of each nutrient in the list, and then calculate the weighted average:

$$\Sigma_{i=1}^{k} w_i S_i(x) \quad (2)$$

Figure 3:
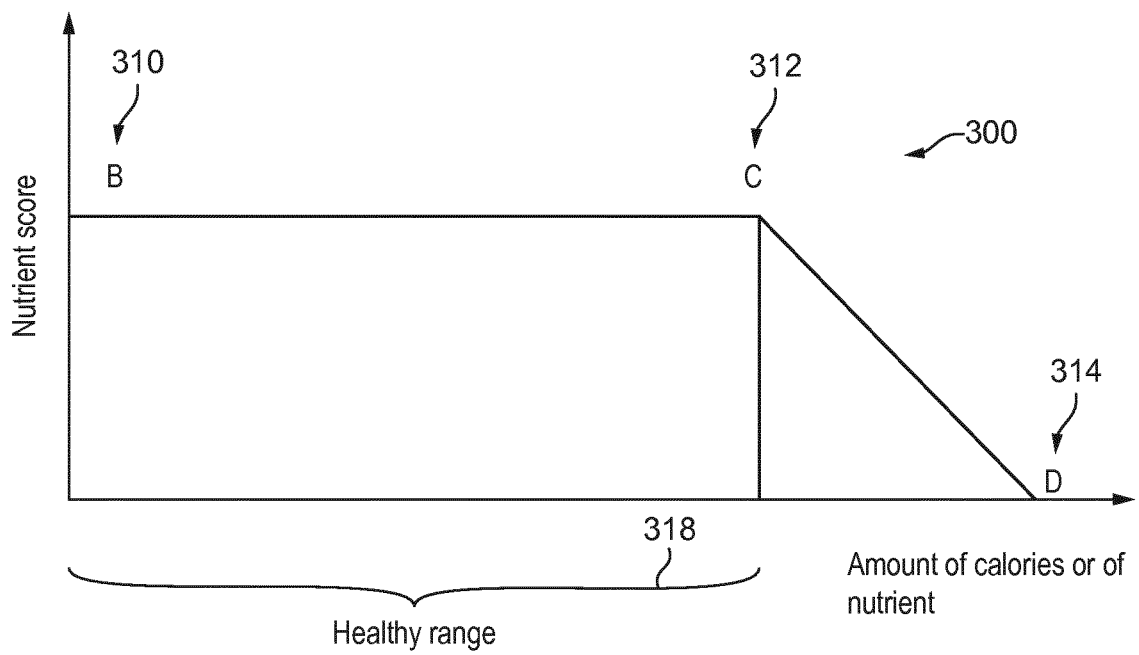
FIG. 3 is an example nutrient scoring graph for a nutrient that cannot be under-consumed, but can be over-consumed.

This will result in a number between 0 and 1, for this example. The weights are numbers $0 \leq w_i \leq 1$, summing up to 1: $\Sigma_{i=1}^{k} w_i = 1$. Note that the formula (1) is not applicable if A=B or if A is not defined. This happens, for example, with saturated fat or added sugar, where there is no minimal recommended amount; in this scenario, consuming none of a particular food item is favorable, and the only unfavorable scenario is consuming too much of the item. An example of this type of scoring function is illustrated in FIG. 3. FIG. 3 represents a scoring function 300 for nutrients having no intake requirement, meaning individuals do not need any amount of these nutrients, but can tolerate a certain amount in their diets. For example, such as can be added sugar, or saturated fat. The function represented in FIG. 3, can be written as:

$$S(x) = \begin{cases} 1 & \text{if } x \leq x_C \\ \dfrac{x_D - x}{x_D - x_C} & \text{if } x_c \leq x \leq x_D \\ 0 & \text{if } x \geq x_D \end{cases}$$

Point B (310) in FIG. 3 is 0, as it represents the lower limit of the healthy range (318 as it demonstrates individuals do not need any of these types of nutrients (i.e., saturated fat, added sugar, etc.) to remain healthy. Point C (312) represents the upper limit of the healthy range (318). Consumption of a nutrient beyond Point C (312) will result in a lower nutrient score. Point D (314) defines a score of 0 when consumption of a nutrient is above the healthy range. Point D (216) is determined with respect to a tolerance for over-consumption of a nutrient. In another embodiment, for some nutrients, the system either assigns an infinite Point C or defines an infinite upper healthy range value to achieve the same outcome—namely, to indicate that overconsumption of a particular nutrient is not harmful. In an alternative embodiment, the score for consuming none of a nutrient such as the example nutrient of FIG. 3 (where none of the nutrient is actually required for a given diet), the nutrient will have a score that is less than 100 but greater than 0. That is, while consuming none of a particular nutrient will not contribute a full potential score (100), the fact that the nutrient is not needed means that consuming none of that nutrient will nonetheless contribute positively to an increased score.

Energy itself is scored according to a similar function as that illustrated in FIG. 2. In particular, with regard to energy, there is a minimum below which the energy score is zero, a range where the contribution to score is increasing, then constant, then decreasing, and a maximum above with the energy score is zero. The Estimated Energy Requirement or "EER" reflected in the equation below is calculated using IOM equation (http://www.nal.usda.gov/fnic/DRI/DRI_Energy/energy_full_report.pdf, page 185).

For example, in a sedentary 40 year old woman, of average height and weight, 162.9 cm and 78.5 Kg respectively (CDC), this would be approximately 1,000 Kcal. Note that for that woman the basal metabolic rate ("BMR") would be approximately 1,442 kcals. Therefore, 1,000 kcal is not a sustainable caloric intake. In this instance, the lower limit for calories is 10% less than the target energy intake. In other embodiments, the lower limit for calories could be other percentages, such as between 15%-50%, depending on the ability of one to accurately input the energy consumed during a time period. The target energy intake is estimated energy expenditure, for example for the sedentary 40 year old woman described above, the IOM provides 2033 Kcal/day, and therefore, the lower limit of a healthy range would be 1830 Kcal/day. The function is represented below, where the acronym "EER" stands for Estimated Energy Requirement:

$$S(E) = \begin{cases} 0 & \text{if } E \leq 0.5 * EER \\ \dfrac{1}{0.4 * EER}(E - 0.5 * EER) & \text{if } 0.5 * EER \leq E \leq 0.9 * EER \\ 1 & \text{if } 0.9 * EER \leq E \leq 1.1 * EER \\ -\dfrac{E - 1.5 * EER}{0.4 * EER} & \text{if } 1.1 * EER \leq E \leq 1.5 * EER \\ 0 & \text{if } E \geq 1.5 * EER \end{cases}$$

Figure 4:
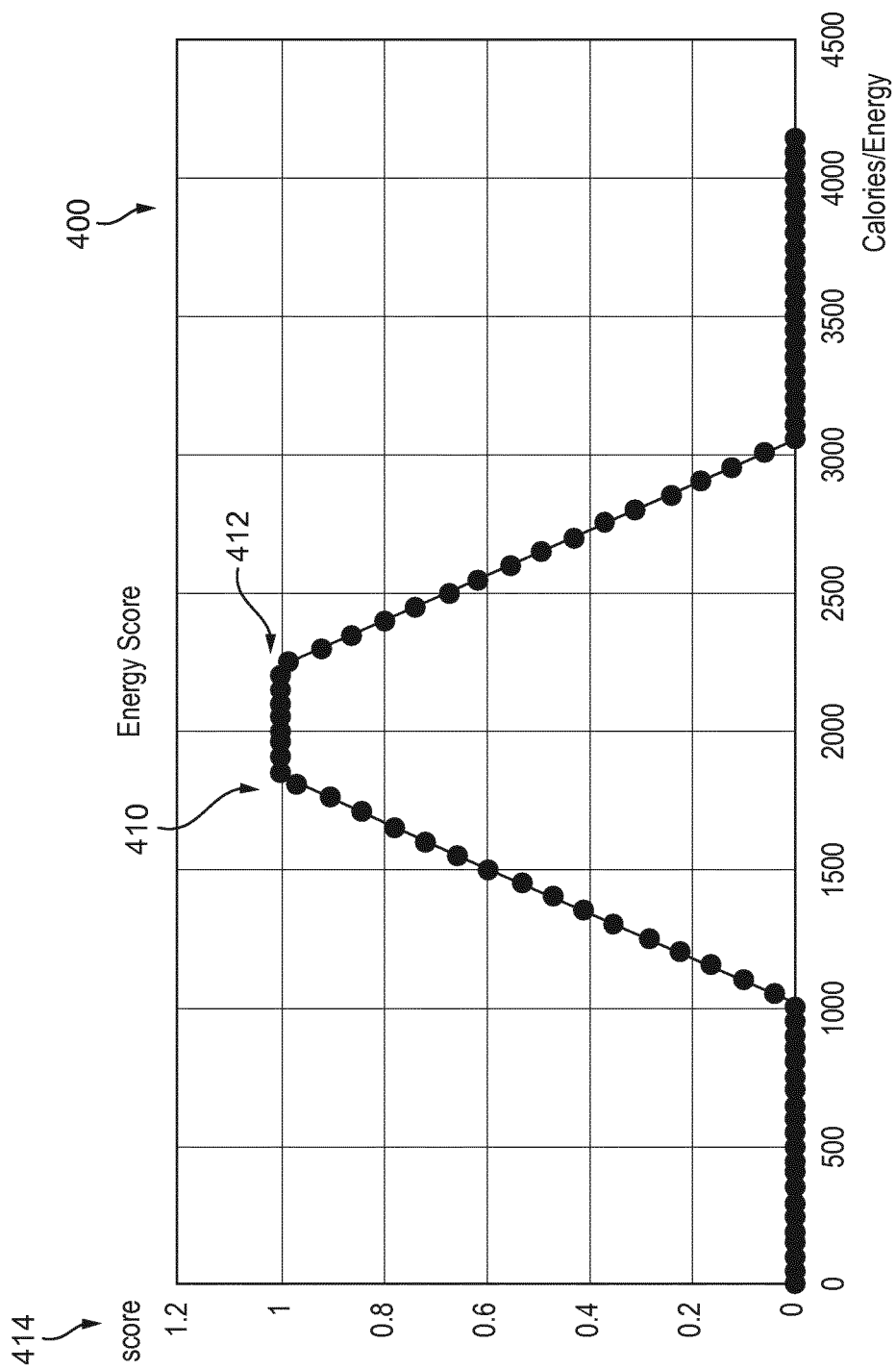
FIG. 4 is an example graph illustrating an energy score for a range of energy consumption amounts.

FIG. 4 depicts this function graphically for an EER=2033 Kcal/day. The EER reflected in FIG. 4 discloses the target energy intake for the woman previously mentioned, is estimated at 2033 Kcal/day, and therefore, the lower limit of a healthy range would be 1830 Kcal/day (410 in FIG. 4). The upper limit for calories is 10% more than the target energy intake. For the woman described above, the upper limit of a healthy range would be 2236 Kcal/day (412 in FIG. 4). A score of zero is given when total energy intake≥(1.5*EER), with BMR being calculated using the IOM formula. This would be approximately 3,000 Kcal for the example woman previously mentioned.

The tolerance of 10% above and below the EER was determined for purposes of the disclosed system and methods based on heuristic and practical considerations, taking into account the typical standard deviation in the EER estimate. The actual EER (and thus the range 10% above and below the EER) depends on several parameters: age, gender, height, weight and physical activity level. In light of a recent publication (Shcherbina et al, *Accuracy in wrist-worn, sensor-based measurements of heart rate and energy expenditure in a diverse cohort*, J. Pers. Med. 2017, 7, 3), this range may be extended in some embodiments. According to the noted study, popular commercial wearable devices have a large error in estimating energy expenditure (>20%), therefore the tolerance range should align with the achievable precision. In a clinical context, however, a higher precision can be attained, so the tolerance for energy should be adapted to the context.

Using the energy score (414) determined consistent with equation 2 and FIG. 4 above (referred to as S(E)), embodiments of the disclosed system and methods determine a final SDIS by multiplying the energy score (414) by the weighted nutrient score reflected in equation (3):

$$S(E) \sum_{i=1}^{k} w_i S_i(x) \tag{3}$$

It should be appreciated that in calculating the final SDIS, the system disclosed herein uses energy as a factor multiplying the average nutrient score. This technique is an improvement on the known prior art because it accurately reflects the importance of the amount of energy consumed to the overall SDIS.

In some embodiments of the system disclosed herein, in addition to the average nutrient score being multiplied by the energy score, energy can also be included in other ways. For example, referring again to FIG. 2, Point B (212) may be selected corresponding to the RDA as defined by the IOM. The RDA is a recommended minimum intake that meets intake requirements for 97.5% of the population. While in some exemplary embodiments the disclosure may discuss or represent the RDA in terms of the quantity (i.e., grams) of a nutrient consumed, it is important to note that other representations, such as percentages, are also useful. Further, in various embodiments, the quantity consumed may be converted to a percentage. In alternative embodiments, RDAs expressed as a percentage may be converted into a quantity consumed. The AI, or other types of recommendations, may be used when the RDA is not available (examples are fiber and potassium). Point A (210) may be chosen based on some percentile of usual intake in a given or chosen population. Point C (214), as indicated previously, is the tolerable upper limit of the healthy range (218). Previously, this has been defined by the IOM. However, the IOM is usually too high, and for some nutrients is even undefined. An undefined upper limit may cause overconsumption of a particular nutrient, with respect to a given energy target, to go undetected. Therefore, Point C (214) in this disclosure does not represent a toxicological value. Rather, it represents a 'reasonable' upper limit in the context of a healthy eating pattern at a given energy level. Therefore, the Points C (214) depends on energy. Therefore, the SDIS is energy-adjusted not only through the energy factor discussed above, but also through the choice of healthy ranges. Point D (216) is chosen based on the amount of the nutrient contained in typical foods rich in that nutrient. In an alternative embodiment, instead of using individual nutrients, a whole food group may be used. In the whole food group example embodiment, the range relates to a recommended intake for an entire food group, as opposed to individual nutrients.

In various embodiments, the parameters of the scoring algorithm are chosen according to a particular measurement goal. For example, the parameters may be different in the context of weight loss versus in the context of a target population that is pre-diabetic. While the previous calculations work with any choice of nutrients, ranges and weights, these choices are important in order for a score to distinguish between healthy and unhealthy eating patterns.

Table 2, below, shows two exemplary iso-caloric menus, with different dietary qualities. Table 2 and FIGS. 5-8, demonstrate that the SDIS correctly distinguishes the healthy menu example from the unhealthy example, as well as demonstrates the relationship between of how quality depends on quantity.

TABLE 2

Two Isocaloric Menus with Different Dietary Qualities

| Combination 1 | Healthy | Unhealthy |
|---|---|---|
| Breakfast | Fruit juice smoothie 227 g | Pork, cured, bacon, pre-sliced, cooked, pan-fried 16 g |
| | Egg, whole, cooked, poached 50 g | Egg, whole, cooked, fried 47 g |
| | Bread, wheat germ, toasted 28.35 g | Bread, white, commercially prepared, toasted 28.35 |
| | Margarine-like, vegetable oil spread, 20% fat, without salt 10 g | Butter, salted 5 g |
| Lunch | Turkey, all classes, light meat, cooked, roasted 108 g | Turkey, drumstick, smoked, cooked, with skin, bone removed 100 g |
| | Cabbage, red, cooked, boiled, drained, without salt 22 g | Restaurant, family style, hash browns 100 g |
| | Carrots, cooked, boiled, drained, without salt 9.7 g | Vegetables, mixed, frozen, cooked, boiled, drained, with salt 50 g |
| | Potatoes, red, flesh and skin, baked 299 g | |

TABLE 2-continued

Two Isocaloric Menus with Different Dietary Qualities

| Combination 1 | Healthy | Unhealthy |
|---|---|---|
| Supper | Fast foods, submarine sandwich, tuna on white bread with lettuce and tomato 239 g | Pizza, pepperoni topping, regular crust, frozen, cooked 190 g |

Figure 5:
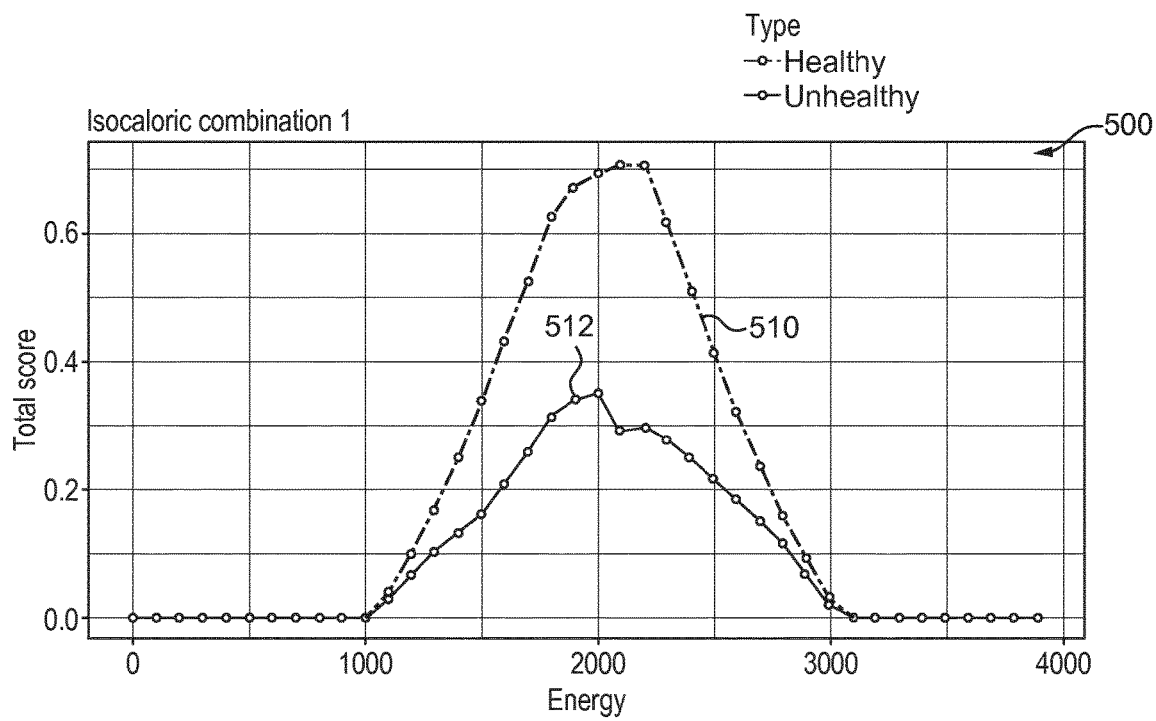
FIG. 5 is an example graph illustrating a score calculated according to embodiments of the disclosed system for a healthy diet versus an unhealthy diet.

For the purposes of this example, the energy requirement is 2000 kcals. FIG. 5 depicts a graph 500 comparing the two example menu plans. FIG. 5 illustrates that the SDIS correctly gives a higher score for the example healthy menu plan, which is the dotted line represented by numeral 510. The unhealthy menu plan is represented by the dotted line represented by numeral 512. FIG. 5 depicts the SDIS depending on a continuum of calories consumed to achieve the nutrients in the menu plan. The menus have been scaled simultaneously at different energy levels (multiplying all the amounts by the same factor), from 0 to 4000 kcals. Then, for each energy level, the score of each menu is plotted (dots in the figure). The scores fall to 0 outside the permissible caloric intake range 1000-3000 because multiplying by an energy score of zero results in an overall SDIS of zero. Between 1000 and 3000 kcals, the healthy menu scores (line 510) is consistently at a higher score than the unhealthy menu. Both curves reach a maximum value at about 2000 kcals, meaning that the amount of food provided by each menu plan provides the optimal amount of the nutrients at that energy level. For any given energy level, the difference in the scores measures their difference in 'quality,' and this difference varies with the energy level (the 'quantity'), reaching a maximum difference at an optimal energy intake of around 2000 calories (the determined EER for the person consuming the menu plans).

Figure 6:
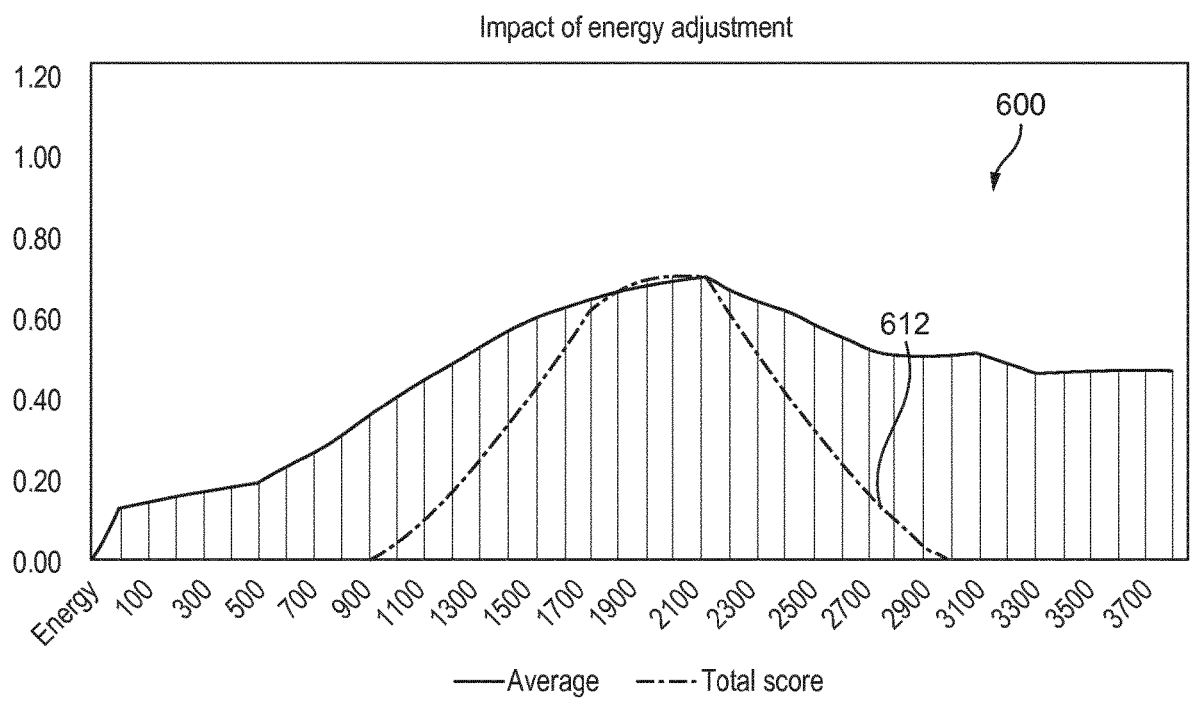
FIG. 6 is an example graph illustrating a score calculated for an energy adjusted curve versus a non-energy adjusted curve.

FIG. 6 depicts a score graph 600 for the healthy menu 612, compared to the average nutrient score 610, without the energy factor. In other words, the line 610 corresponds to only the average nutrient score $\Sigma_{i=1}^{k} w_i S_i(x)$, while the line 612 is $S(E)*\Sigma_{i=1}^{k} w_i S_i(x)$, the SDIS. FIG. 6 illustrates the importance of the energy factor to control calorie levels that are not physiologically plausible or desirable—in the context of a person whose EER is around 2000 calories, that person still receives a non-zero score for caloric intakes nearly double the recommended intake. Indeed, this non-zero score is approximately 0.45, not far below the optimal score of near 0.65 at a 2000 calorie intake.

Figure 7:
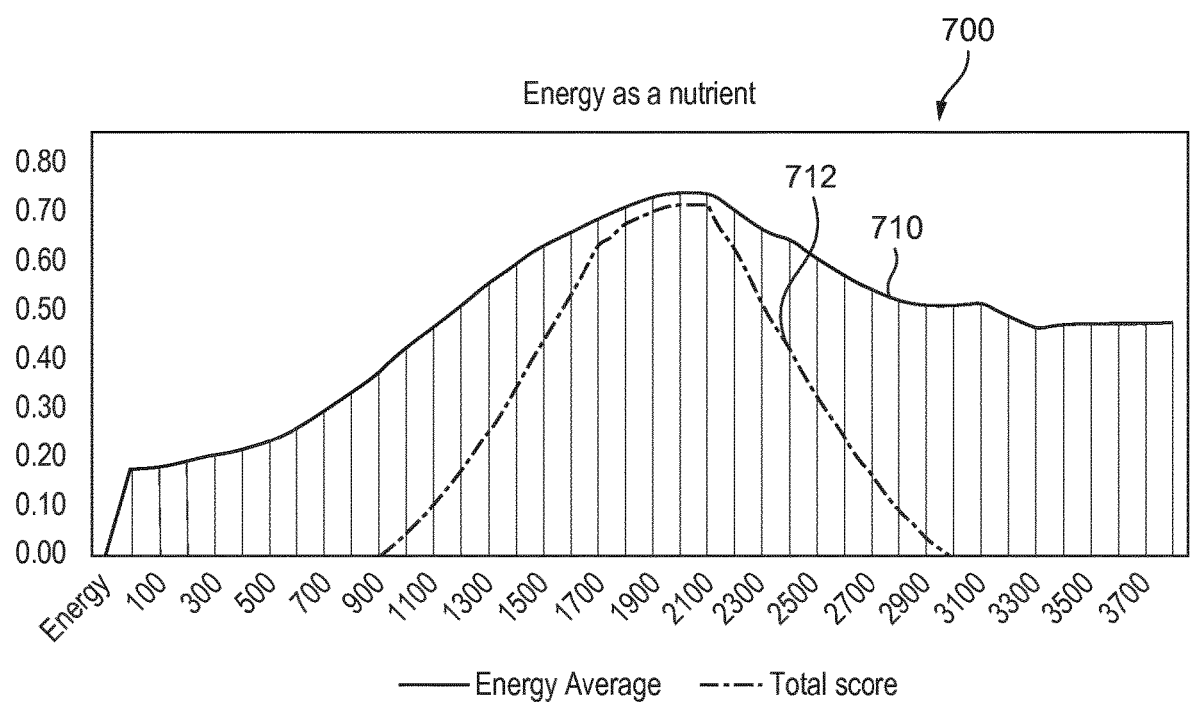
FIG. 7 is an example graph based on this disclosure of an energy adjusted curve versus a curve where energy is treated as a nutrient.

FIG. 7 illustrates a scoring function according to the present disclosure where energy is factored into the SDIS by multiplication (line 712), versus a scoring function according to a technique where energy is averaged into the score just as any other nutrient would be (line 710). Comparing FIG. 6 and FIG. 7, it can be seen that the top lines (line 610 in FIG. 6, and line 710 in FIG. 7), where energy is either ignored (FIG. 6) or averaged into the score (FIG. 7) are nearly identical. This indicates that energy has little impact on the total score if it averaged together with all the nutrients. Indeed, the more nutrients are averaged into the score, the smaller the impact of energy on the overall average. This comparison shows the importance of one of the improvements recognized herein: that energy should be factored into the SDIS not as another nutrient to be averaged, but rather as a multiplier, to reflect its importance to the overall score.

Figure 8:
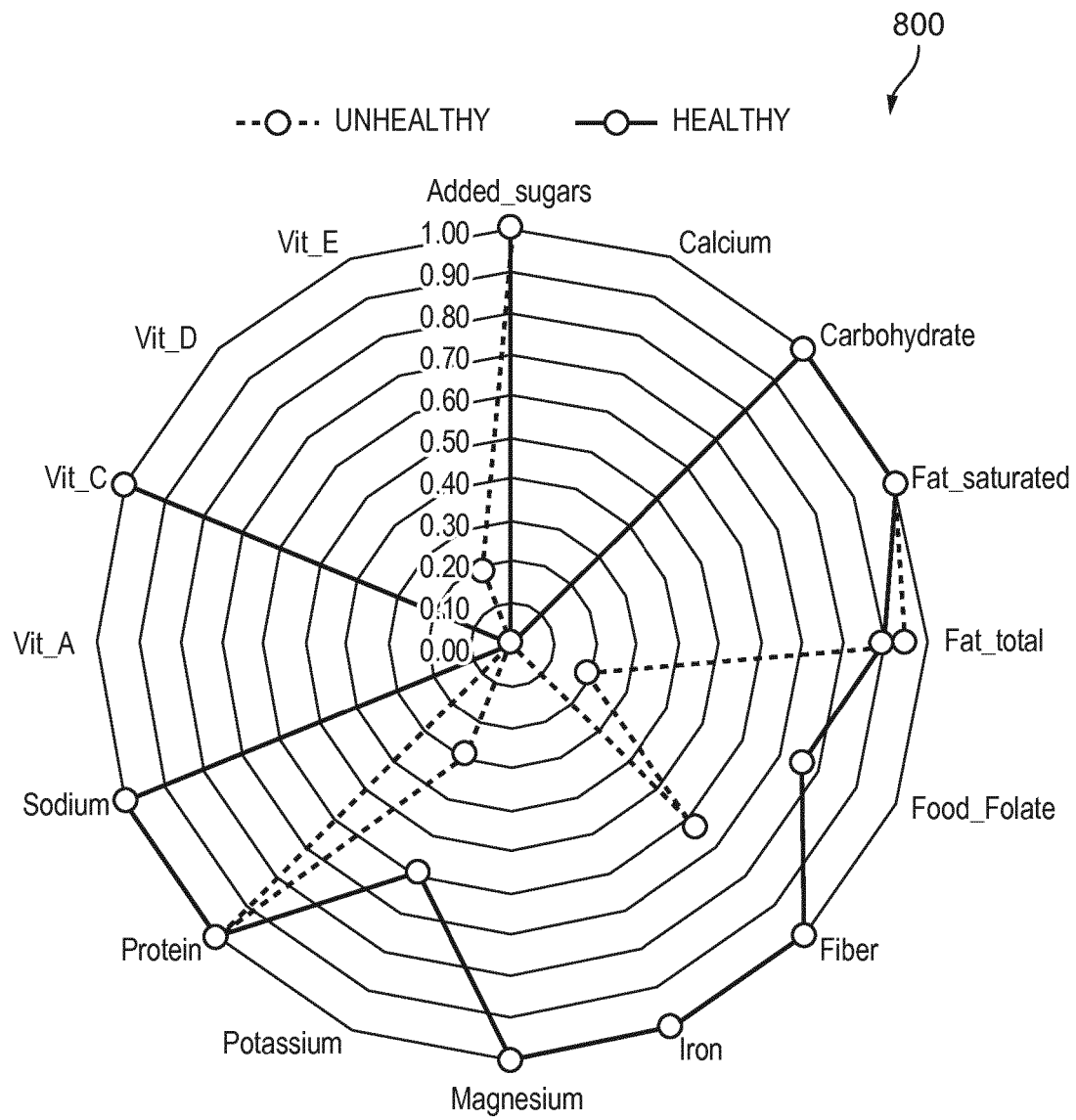
FIG. 8 is an example graph of individual nutrient scores for a healthy diet versus an unhealthy diet.
Figure 9:
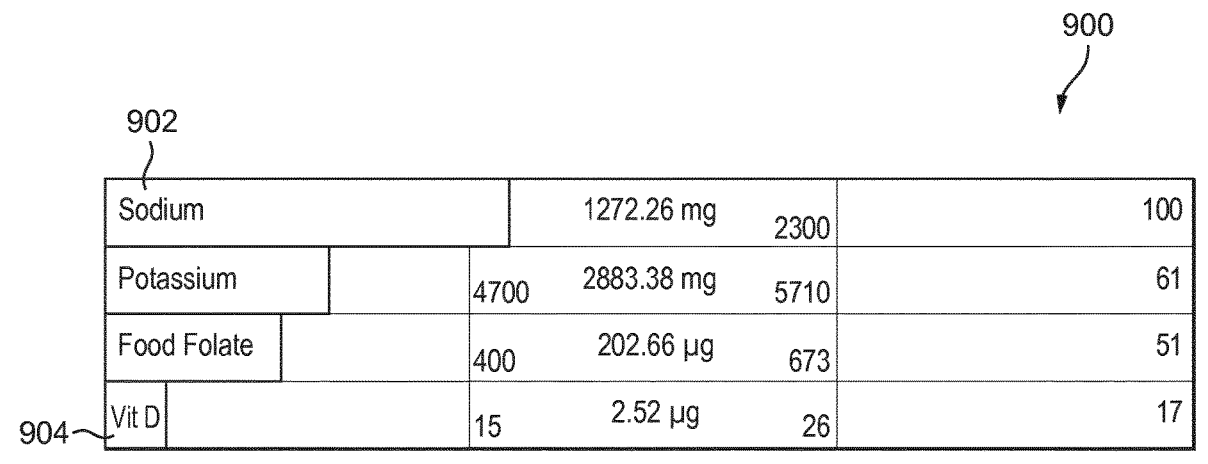

FIG. 8 depicts an example graph 800 that compares the individual nutrient scores, on a nutrient-by-nutrient basis, for the healthy and unhealthy diets, at 2000 kcals based on the diets disclosed in Table 1. The graph 800 depicts the largest differences for Vitamins C, Iron, Sodium, Magnesium and Folate. These are known as micronutrients of concern for public health. The graph 800 fails to clearly identify whether these differences correspond to an under- or over-consumption of these nutrients. This type of information would be visually represented in an app or user interface. An example of how this information could be communicated to a user can be seen in FIG. 9. FIG. 9 depicts an example display 900 of a software application correlating to the SDIS. Example display 900 displays an example bar graph for a few nutrients. The display 900 depicts that the individual has consumed 1272.26 mg of sodium (902), which the app gives a score of 100. However, the individual has received a score of only 17 for the vitamin D (908).

Below is Table 3 depicting an example nutrient composition of an example menu suggested by this disclosure: this example table can be used to estimate the healthy ranges, based on an illustrated fortified and unfortified version of recommended menu plan.

TABLE 3

Nutrient Composition of a Menu

| Nutrients | Example Menu- unfortified | | | | Example menu - fortified | | | |
| --- | --- | --- | --- | --- | --- | --- | --- | --- |
| | Mean | Standard Deviation | Minimum | Maximum | Mean | Standard Deviation | Minimum | Maximum |
| Energy Kcal/day | 2093.8 | 211.5 | 1870.7 | 2464.4 | 2103.5 | 225.7 | 1870.7 | 2509.9 |
| Carbohydrate (% energy intake) | 54.46 | 7.47 | 46.9 | 67.98 | 54.78 | 7.54 | 46.9 | 67.98 |
| Protein (% energy intake) | 19.38 | 3.11 | 16.65 | 24.86 | 19.27 | 3.15 | 16.65 | 24.86 |
| Total fat (% energy intake) | 28.62 | 6.96 | 16.14 | 35.92 | 28.4 | 7.04 | 16.14 | 35.69 |
| Saturated fat (% energy intake) | 6.62 | 2.281 | 3.026 | 9.22 | 6.545 | 2.195 | 3.026 | 9.22 |
| Calcium mg/day | 1449 | 271 | 1090 | 1900 | 1539 | 409 | 1090 | 2200 |
| Food Folate µg/day | 447.5 | 173.2 | 202.2 | 673.1 | 439.1 | 171.1 | 202.2 | 673.1 |
| Fiber (g) | 31.39 | 3.27 | 27.47 | 35.2 | 31.42 | 3.29 | 27.72 | 35.2 |
| Iron mg/day | 17.74 | 5.13 | 11.88 | 26.35 | 17.7 | 5.1 | 11.98 | 26.35 |
| Magnesium mg/day | 507.1 | 64.4 | 392.3 | 558.5 | 506.6 | 64 | 392.3 | 558.5 |
| Potassium mg/day | 4891 | 494 | 4331 | 5710 | 4873 | 470 | 4355 | 5612 |
| Sodium mg/day | 1925 | 341 | 1359 | 2531 | 1974 | 348 | 1391 | 2590 |
| Vitamin A µg/day | 1127 | 535 | 631 | 2250 | 1206 | 554 | 631 | 2250 |
| Vitamin C mg/day | 173.3 | 98.4 | 57.4 | 346.7 | 161.9 | 88.6 | 57.4 | 305.9 |
| Vitamin D µg/day | 9.07 | 7.6 | 4.12 | 26.06 | 11.89 | 6.49 | 7.3 | 26.06 |
| Vitamin E µg/day | 10.02 | 3.75 | 6.05 | 16.83 | 10.81 | 4.6 | 6.15 | 19.54 |
| Added sugars (% energy intake) | 5.39 | 3.11 | 0.5 | 9.09 | 5.39 | 3.11 | 0.5 | 9.09 |

It is important to note that the SDIS is not an additive function. In particular, adding a 'healthy' food to a healthy menu can potentially decrease the total score. This will happen if the energy or some nutrients exceed their upper limits. On the other hand, adding an 'unhealthy' food in small amount might in some cases improve the score. Therefore, quality and quantity are intertwined and should not be considered separately. In addition, it will be appreciated that our score may be used to measure the healthiness of the whole diet, and is not limited to a single food or meal. However, the described techniques and SDIS may be applied to any amount of food consumption and is therefore customizable. Although the SDIS may be most useful for viewing eating patterns over the course of a week, it can also be highly useful for any amount of food, or any time range. For example, with regard to food consumption the SDIS could be used to from a single bite to the amount of food consumed over the course of years. Similarly, the SDIS may be modified for any time range including seconds, minutes, hours, days, weeks, months, years, etc.

Further, although nutrient-dense foods are certainly an essential component of any healthful diet, there is enough flexibility in a diet to allow for some (small) amounts of less nutrient-dense foods in the context of a healthy diet. This is in accordance with the Dietary Guidelines for Americans 2015-2020: "Calories up to the limit for the specific pattern can be used to eat foods that are not in nutrient-dense forms (e.g., to accommodate calories from added sugars, added refined starches, or solid fats) or to eat more than the recommended amount of nutrient-dense foods." Although the embodiments discussed throughout this disclosure reference primarily US RDAs, the scope of this disclosure encompasses or envisions the use of RDAs from different countries, not only the US.

Table 4 is from the validation paper on HEI 2005. This table shows a recommended food groups, expressed per 1,000 kcal, and discretionary calorie allowances, expressed as a percentage of total calories. Table 4 depicts that the amount of the various food groups to consume, although similar, is not identical across energy levels. Therefore, in a density approach to dietary intake, one generally must choose a recommended amount of a nutrient corresponding to a specific energy level. This would produce inaccuracy when applied to a different level. The disclosure stated herein is not based purely on a density approach to dietary intake, and therefore does not suffer from this problem.

TABLE 4

Recommended food groups expressed per calorie level

| Food group | Calorie level | | | | | | | | | | | |
|---|---|---|---|---|---|---|---|---|---|---|---|---|
| | 1000 | 1200 | 1400 | 1600 | 1800 | 2000 | 2200 | 2400 | 2600 | 2800 | 3000 | 3200 |
| Fruits (cup eq/1000 kcal) | 1.0 | 0.8 | 1.1 | 0.9 | 0.8 | 1.0 | 0.9 | 0.8 | 0.8 | 0.9 | 0.8 | 0.8 |
| Vegetables (cup eq/1000 kcal) | 1.0 | 1.3 | 1.1 | 1.2 | 1.4 | 1.3 | 1.4 | 1.3 | 1.4 | 1.3 | 1.3 | 1.3 |
| Dark green vegetables | 0.1 | 0.2 | 0.2 | 0.2 | 0.2 | 0.2 | 0.2 | 0.2 | 0.2 | 0.2 | 0.1 | 0.1 |
| Orange vegetables | 0.1 | 0.1 | 0.1 | 0.1 | 0.2 | 0.1 | 0.1 | 0.1 | 0.1 | 0.1 | 0.1 | 0.1 |
| Legumes | 0.1 | 0.1 | 0.1 | 0.2 | 0.2 | 0.2 | 0.2 | 0.2 | 0.2 | 0.2 | 0.2 | 0.2 |
| Starchy vegetables | 0.2 | 0.3 | 0.3 | 0.2 | 0.2 | 0.2 | 0.4 | 0.4 | 0.4 | 0.4 | 0.4 | 0.4 |
| Other vegetables | 0.6 | 0.5 | 0.5 | 0.5 | 0.5 | 0.5 | 0.5 | 0.4 | 0.5 | 0.4 | 0.5 | 0.5 |
| Grains (oz eq/1000 kcal) | 3.0 | 3.3 | 3.6 | 3.1 | 3.3 | 3.0 | 3.2 | 3.3 | 3.5 | 3.6 | 3.3 | 3.1 |
| Whole grains | 1.5 | 1.7 | 1.8 | 1.9 | 1.7 | 1.5 | 1.6 | 1.7 | 1.7 | 1.8 | 1.7 | 1.6 |
| Other grains | 1.5 | 1.7 | 1.8 | 1.3 | 1.7 | 1.5 | 1.6 | 1.7 | 1.7 | 1.8 | 1.7 | 1.6 |
| Milk (cup eq/1000 kcal) | 2.0 | 1.7 | 1.4 | 1.9 | 1.7 | 1.5 | 1.4 | 1.3 | 1.2 | 1.1 | 1.0 | 0.9 |
| Meat and Beans (oz eq/1000 kcal) | 2.0 | 2.5 | 2.9 | 3.1 | 2.8 | 2.8 | 2.7 | 2.7 | 2.5 | 2.5 | 2.3 | 2.2 |
| Oils (g/1000 kcal) | 15.0 | 14.0 | 12.0 | 14.0 | 13.0 | 14.0 | 13.0 | 13.0 | 13.0 | 13.0 | 15.0 | 16.0 |
| Discretionary calories (%) | 16.5 | 14.3 | 12.2 | 8.3 | 10.8 | 13.4 | 13.2 | 15.1 | 15.8 | 15.2 | 17.1 | 20.3 |

Figure 10:
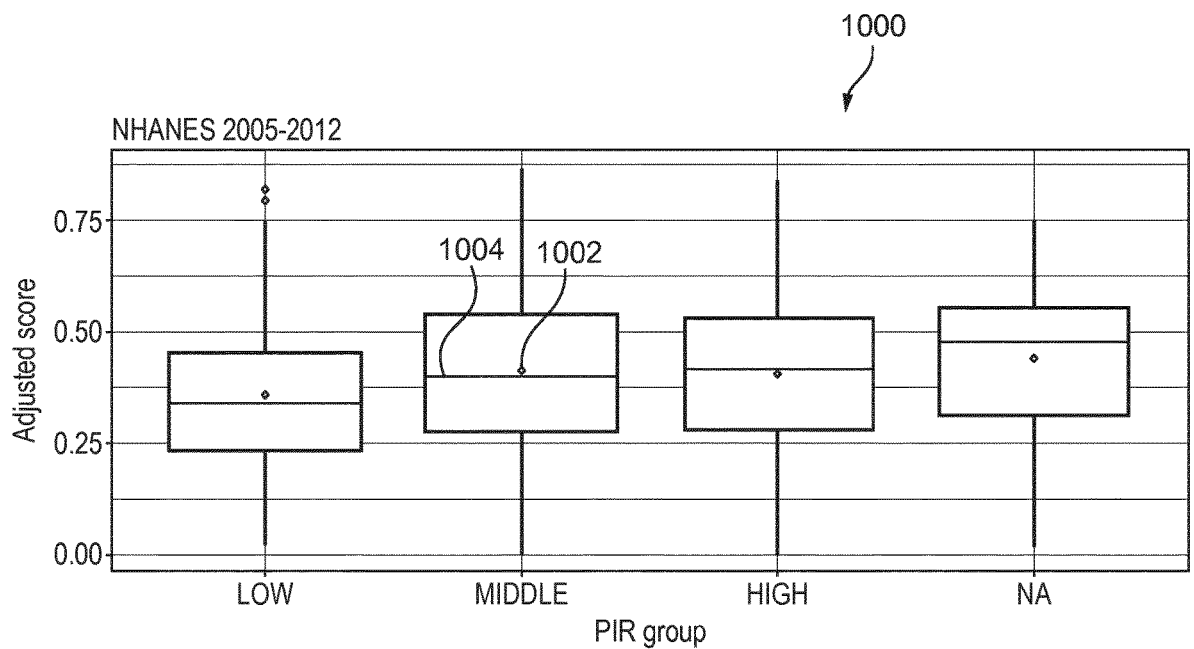
FIG. 10 is an example graph based on this disclosure of using the SDIS to determine the correlation between poverty and nutrition.

The SDIS can be usefully applied, for example, at the level of a population or to various groups of people. This may be useful to detect deficiencies, deviations from healthy eating patterns, and more generally to detect any pattern at the population level. As an example, FIG. 10 depicts an example graph 1000 displaying the results of a study conducted regarding the correlation between diet quality and income level. The study focused on women in the age group 31-50. The diamond markers (1002) correspond to the mean value of the results. The horizontal middle line (1004) corresponds to the median. Subjects were grouped according to Poverty to Income Ratio (PIR). A low PRI was defined as less than 1.3, a middle PRI was defined as between 1.3 and 3.49, and a high PRI was defined as greater than 3.5. Similarly, instead of income level, the SDIS may be used to investigate any other covariate, including biological measurements.

Figure 11:
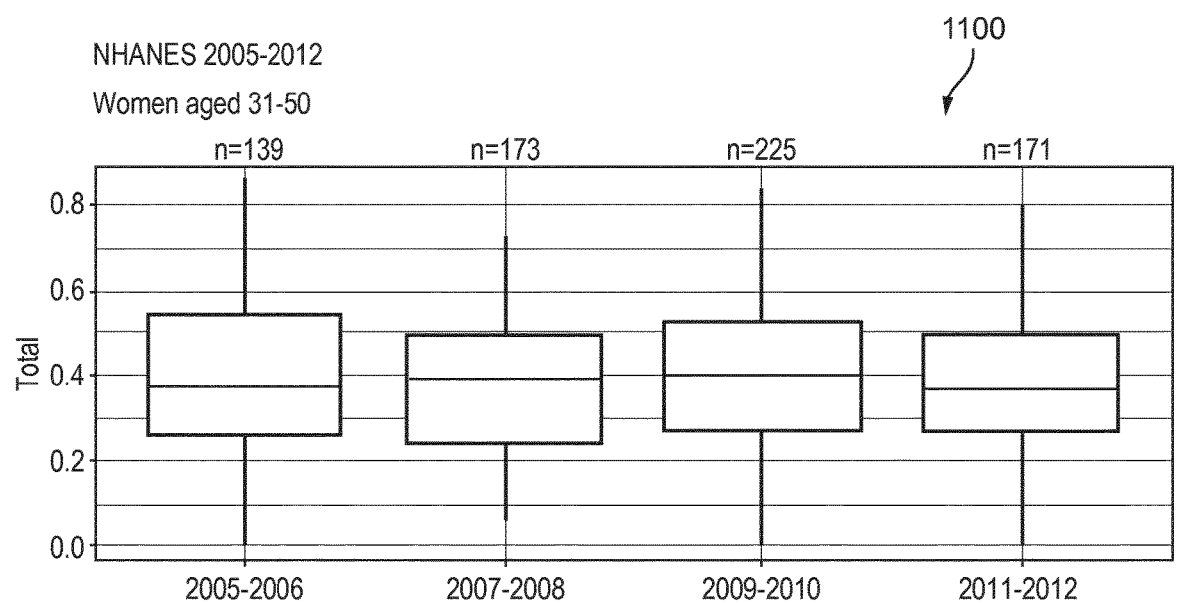
FIG. 11 is an example graph based on this disclosure of using the SDIS to measure historical trends.

Another possible application of the SDIS is depicted in FIG. 11. FIG. 11 is an example graph 1100 showing the evolution of the SDIS in a specific population over a period of time. For example, FIG. 11 shows a time range from 2005 to 2012. As can be seen from graph 1100, the difference is minimal, implying that in this example no real improvement has taken place in the eating habits over the course of that time period.

Another possible application of the SDIS is the comparison of different eating patterns. For example, a comparison may be conducted for eating patterns of vegetarian, US-style of consumption, the Mediterranean style of consumption, etc. FIG. 12 depicts a table as an example, with SDISs calculated for each of the tracked eating styles. The example table 1200 demonstrates the eating patterns discussed have relatively equivalent scores. Column 1210 represents 16 of the most important nutrients, although other nutrients may be included, in composing the SDIS score. Column 1210 also includes a row for energy. Column 1212 represents a lower caloric intake (lower energy intake) than column 1214. Column 1214 represents a lower caloric intake than column 1216. Looking at columns 1212, 1214, and 1216, a minor improvement in score can be seen in column 1216 at the higher caloric content for some of the diets, due to higher intakes of potassium, iron and vitamin E. As can be seen from Table 5 below, the three healthful dietary patterns that are recommended in the 2015 US dietary guidelines all scored an SDIS score ≥0.87 at 3 different energy levels. This demonstrates that the recommendations in all three dietary patterns result in the same nutrient composition (despite being different foods). Further, this demonstrates the accuracy and reliability of the SDIS score. It should be appreciated that in some embodiments, other benefits of a diet (outside of the 16 measured nutrients in the preferred embodiments of the system and methods disclosed) will be taken into account such that a score for the Mediterranean diet, for example, is increased to account for benefits particular to that diet despite having a same output of the SDIS function.

TABLE 5

Three healthy diets with SDIS scores

| | Mediterranean | Vegetarian | US-style |
|---|---|---|---|
| Energy (Kcal) | 1802 | 1826 | 1797 |
| SDIS | 0.88 | 0.89 | 0.87 |
| Energy (Kcal) | 1998 | 2028 | 2003 |
| SDIS | 0.89 | 0.89 | 0.89 |
| Energy (Kcal) | 2203 | 2230 | 2198 |
| SDIS | 0.91 | 0.87 | 0.91 |

Table 6 provides a rationale summary of the healthy ranges for nutrients used in an example SDIS for a female between the ages of 31-50 years old.

TABLE 6

Healthy ranges for nutrients for a female between ages 31-50 years old

| Nutrients | Rationale for zero score | Lower limit of zero score | Lower limit of healthy range | Upper limit of healthy range | Upper limit of zero score | Rationale for zero score |
|---|---|---|---|---|---|---|
| Carbohydrate (% energy) | 25$^{th}$ percentile of NHANES | 27.9 | 45.0 | 67.98 | 72 | 97.5th percentile of NHANES |
| Protein (% energy) | | 7.7 | 10.0 | 24.86 | 29.6 | |
| Total fat (% energy) | | 15.9 | 20.0 | 35.92 | 50.3 | |
| Fiber (g) | 25$^{th}$ percentile of RDA | 10.6 | 25.0 | 38.2 | 45.83 | 7.63 g fibre per portion of high fibre food |
| Calcium mg/day | 25$^{th}$ percentile of RDA | 655 | 1000.0 | 2200 | 2500 | UL = 2500 |
| Potassium mg/day | 25$^{th}$ percentile of RDA | 1863 | 4700.0 | 5710 | 6497.5 | 787.5 g potassium per portion of high potassium food |
| Magnesium mg/day | 25$^{th}$ percentile of RDA | 207 | 320.0 | 641 | 755.66 | 114.6 g magnesium per portion of high magnesium food |
| Iron mg/day | 25$^{th}$ percentile of RDA | 10.5 | 18.0 | 26.3 | 34.38 | 8.08 g iron per portion of high iron of high iron food |
| Food Folate µg/day | 25$^{th}$ percentile of RDA | 144 | 400.0 | 673.1 | 768.9 | 95.81 g food folate per portion of high folate food |
| Vitamin A µg/day | 25$^{th}$ percentile of RDA | 378 | 700.0 | 2802 | 3000 | UL = 3000 |
| Vitamin C mg/day* | 25$^{th}$ percentile of RDA | 40.1 | 75.0 | 346.7 | 463.67 | 116.97 g vitamin C per portion of high vitamin C food |
| Vitamin D µg/day | 25$^{th}$ percentile of RDA | 2.5 | 15.0 | 26.06 | 39.22 | 13.16 g vitamin D per portion of high vitamin D food |
| Vitamin E µg/day | 25$^{th}$ percentile of RDA | 5.0 | 15.0 | 24.06 | 32.34 | 8.28 g vitamin E per portion of high vitamin E food |
| Sodium mg/day | N/A | N/A | N/A | 2590.4 | 3273.73 | 683.33 g sodium per portion of high sodium food. Upper limit is 2.3 g/day but most of the population exceed this. |
| Saturated fat (% energy) | N/A | N/A | N/A | 9.22 | 10 | US Dietary Guidelines 2015-20 https://health.gov/ dietaryguidelines/ 2015/guidelines/ chapter-1/a-closer-look-inside-healthy-eating-patterns/ |
| Added sugars (% energy)‡ | N/A | N/A | N/A | 9.09 | 10 | US Dietary Guidelines 2015-20 https://health.gov/ dietaryguidelines/ 2015/guidelines/ chapter-1/a-closer-look-inside-healthy-eating-patterns/ |

*All individuals; For added sugars https://epi.grants.cancer.gov/diet/usualintakes/pop/2007-10/table_a40.html The chart depicts the lower limit of a zero score, lower limit of the healthy range, upper limit of the healthy range, and upper limit of a zero score for the various nutrients based on an example female between the ages of 31-50. Further, the chart includes the reasons for why these values have been chosen. However, for nutrients such as sodium, added sugars, and saturated fats there is no lower limit of a zero score and lower limit of the healthy range. This is because consumption of these nutrients is tolerable in a diet up to a certain point. For example, sodium is allowable, and generally considered not harmful, up to 2590.4 mg/day. After this, the nutrient score will decrease from the maximum score for the sodium nutrient until it reaches 3273.73 mg. At 3273.73 mg, the score for sodium will become zero. For such nutrients, the system disclosed herein is configured to evaluate adequacy of nutrient intake in terms of maximal amounts.

As a further example, the score might be used with longitudinal data to investigate causal relationships between diet and some health indicator.

Figure 13:
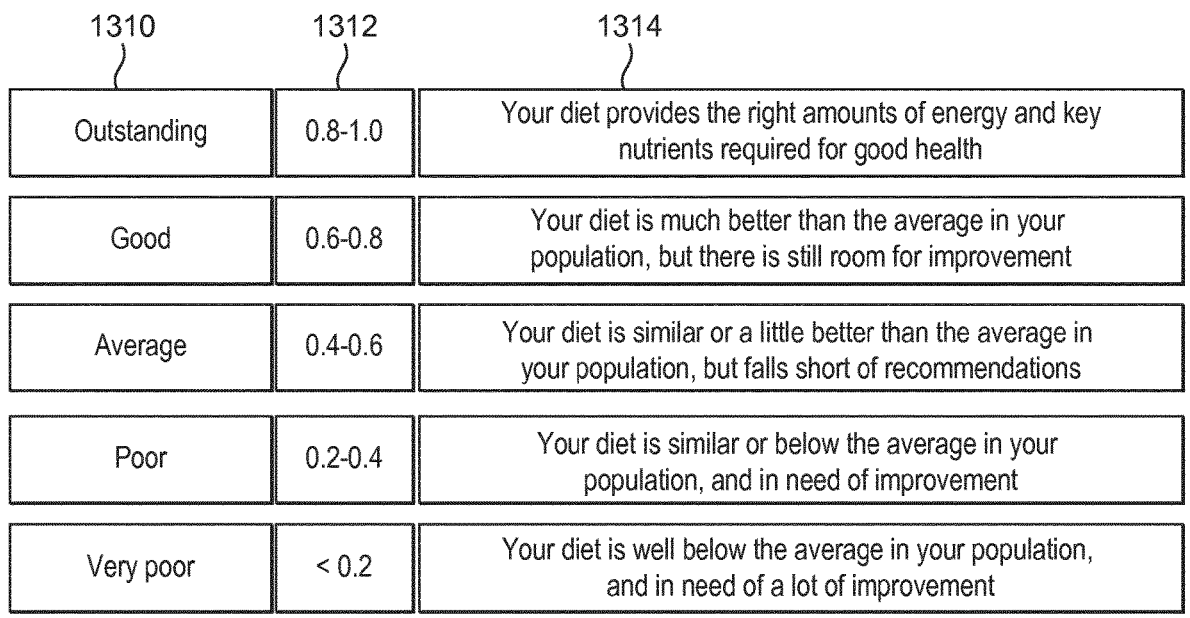
FIG. 13 is an example graphical user interface showing graphical illustrations of SDISs in an embodiment of the system disclosed herein.

Further, the SDIS score can be represented in a mobile or web application, to personalize a user's dietary intake. For example, by obtaining knowledge about the user's eating habits, goals, food preferences, food cost, and sustainability the app can provide the user specific suggestions according to the user's goals. After the user enters their diet, the user can see their SDIS and rate their SDIS according to the example categories in FIG. 13. FIG. 13 depicts an example score chart 1300 that may be presented to a user in an application. The chart 1300 would have a column for the rating (1310), a column for the SDIS score (1312), and a column for explanation (1314). In an example situation where the individual received an SDIS score indicating room for improvement, the app can suggest specific actions for improvement. For example, the app could suggest limiting the amount of certain foods consumed, or adding another food to the diet in order to improve the SDIS. These suggestions can be based on foods that user has already eaten, but also takes into consideration a user's dietary preferences, restrictions, user goals, and contextual information (occasion, seasonality, location).

Figure 15:
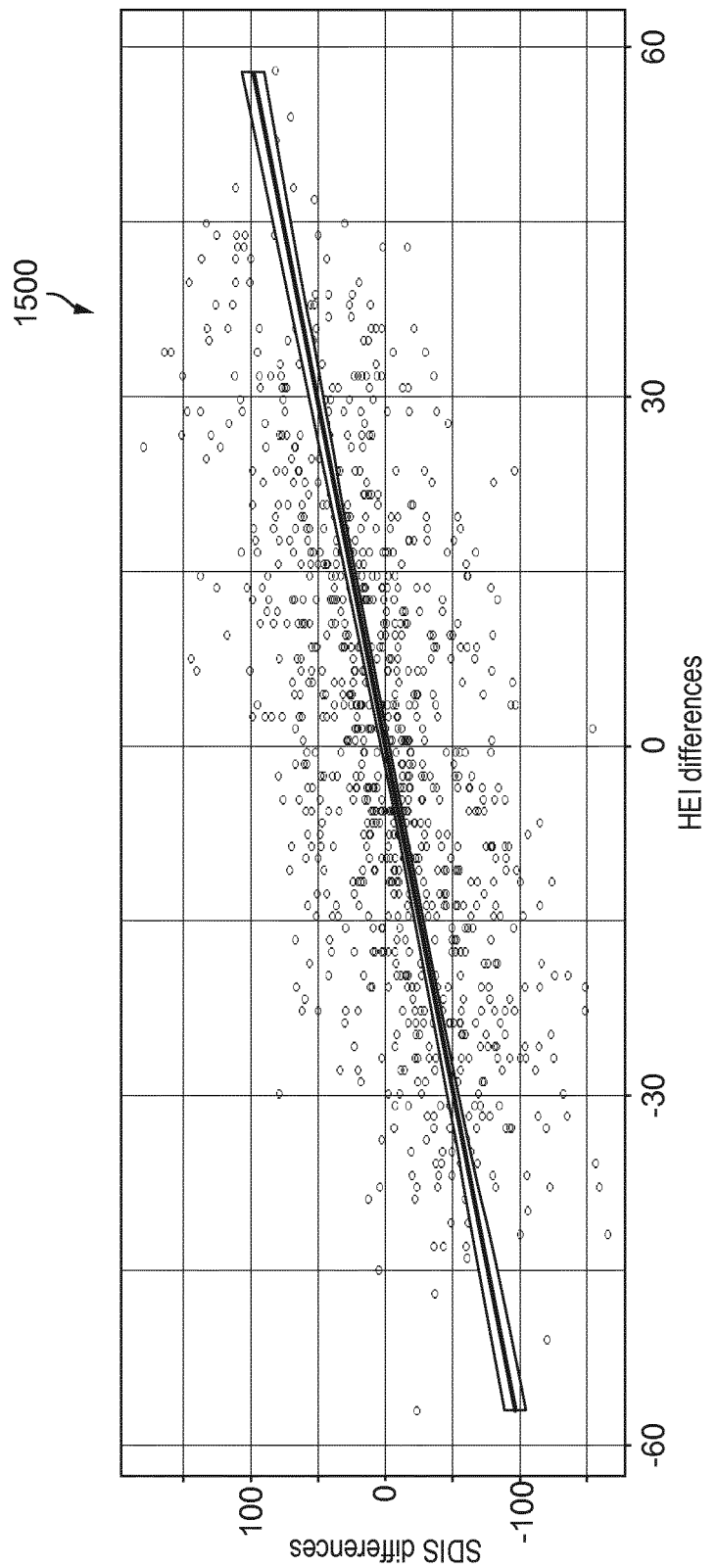
FIG. 15 is an example of pairs of menus comparing differences of HEI scores with differences of SDIS scores.

A study to verify the SDIS was conducted and the reliability of the scores presented in this disclosure were assessed using principal component analysis and Cronbach's coefficient alpha. Validity was evaluated by comparing the scores for healthy and unhealthy isocaloric menu plans across a range of energy levels, and by comparing scores with the HEI results 24 h dietary recalls extracted from NHANES 2011-12. All "menus" in the range of 1800-2200 Kcal consumed by women aged 31-50 years were extracted, which provided 173 data sets. The HEI scores were calculated per individual (cf. https://epi.grants.cancer.gov/hei/tools.html). FIG. 14 depicts the HEI scores of the food combinations. The SDIS score of a healthy food combination, (HEI score of 95) was compared against an unhealthy food combination (HEI score of 15). In chart 1400, column 1410 represents high HEI food combination. Column 1412 represents a low HEI food combination. Further, a comparison of the overall distributions of scores was conducted. 97 pairs of "menus" were randomly sampled and compared the differences of HEI scores with the differences of SDIS scores. An example visualization in FIG. 15 depicts the degree of agreement between the two scores.

In addition, the score was applied to the nutrient composition of three dietary patterns that are recommended in the 2015 US dietary guidelines. In order to demonstrate the applicability of the score to national nutrition survey data, it was applied to NHANES data from 2005-2011 for the above subpopulation of women. The score could discriminate between healthy and unhealthy menu plans, with energy becoming an important determinant when energy was less than or greater than 10% of the estimated energy requirements. The score showed qualitatively good agreement with the mean scores for NHANES data using the Healthy Eating Index, as well as a similar pattern of distribution from the mean. Principal component analysis showed that at least 14 nutrients explain 95% of the variance in the total score. Cronbach's alpha coefficient was 0.73, indicating that the score is reliable. The scores for the three dietary patterns recommended by the US Dietary Guidelines were all high (>0.87), which is comparable to the 2 example healthy menu plans. Application of the algorithm to a subpopulation of NHANES data from 2005-2011, suggested that there was no change in overall diet quality over that time period.

In an alternative embodiment, the disclose system uses the amount of food in the various food groups to set ranges (the ranges being the weight or volume of food in each group (e.g., fruits required for 1000-3200 kcal)) The ranges in this embodiment would be similar to Table 4 above except expressed per day and not per 1000 kcal. This would mean that no energy correction would be needed in the range of 1000-3200 kcal. One advantage of this alternative embodiment is that the SDIS calculation methodology takes into account the whole mixture of nutrients, including bioactives, that are not in the limited list of 16 nutrients. In another alternative embodiment, the disclosed system uses the amount of food in various food categories to set ranges. These food categories may include, for example, categorizations such as snacks, baked products, soft drinks, soups and sauces, frozen foods, canned foods, etc.

In various embodiments, one or more of these inputs (entered food or diet) is pulled from a database of nutritional information. For example, the list of consumed nutrients may be generated in certain embodiments by allowing a user to enter a consumed item and looking up a listing of nutrients contained in that consumed item in an appropriate consumables database. In other embodiments, users enter consumed nutrients directly. In still other embodiments, a user enters a food (e.g., a hamburger) and if that food is not within a database, the user also enters an amount of nutrients within that food (e.g., an amount of sodium). Thereafter, future entries of the defined food (e.g., a hamburger) can lookup nutrients entered at a previous time rather than requiring the user to re-enter the nutrient information.

A user goal, for example, may be to lose weight, to maintain lost weight, to eat a healthy diet, to gain weight, to eat a diet recommended for heart health, etc. In each case, the app may be adapted by changing for example, importance (weights) of its components, component ranges or even a list of used components. For example, if a user wants to lose weight, and his basic energy needs are 2000 kcals, he must eat 1500 kcals per day. In this example, the allowed healthy range for energy will be narrowed and shifted down towards the lower caloric intake. Besides calories, the recommendations formulated by the app will still take care to ensure that user is consuming all other nutritional needs for macro- and micronutrients. Therefore, in this disclosure energy is not considered as a nutrient, but rather energy permeates the entire framework of dietary recommendations and influences the definition of the healthy ranges.

Sometimes it is interesting to look at the individual nutrient scores in a diet, to detect the most problematic ones. Software can be used to then identify the recommended shifts needed in the diet in order to get closer to the recommended amounts. In some embodiments, the system and methods disclosed herein can be used by nutritionists, health-care professionals, and individual users (e.g., users of wearable devices such as smart watches or fitness trackers). In an exemplary embodiment, the system disclosed herein includes at least one processor configured to execute an algorithm to calculate a single score for measuring health through good nutrition over a period of time. In this embodiment, the algorithm takes into account factors specific to an individual (or population of individuals) and determines the score based on a plurality of nutrients within that individual's (or population's) diet in relation to the total energy consumed.

In various embodiments, the user-specific (or population-specific) inputs to the disclosed system are programmable and configurable, and include gender, age, weight, height physical activity level, whether pregnant or lactating, and the like.

In an embodiment, the disclosed system includes or is connected to a database containing foods or food composition items and respective nutrient content. In this embodiment, the disclosed system includes a fuzzy search feature that enables a user to enter a consumed (or to-be consumed) food, and thereafter searches the database to find a closest item to the user-provided item. The disclosed system, in this embodiment, uses stored nutritional information about the matched food item to determine a score as described below.

In various embodiments, the disclosed system further includes an interface (e.g., a graphical user interface) to display the amount of each nutrient available in each food composing the diet, and displays the amount of energy available to be consumed. In some embodiments, this interface enables users to modify the amount of various foods or energy to be consumed, and correspondingly displays an SDIS based on the modified amount of food or energy to be consumed. In other embodiments, the system is configured to determine amounts of food or energy consumed using non-user-input data, such as by scanning one or more bar codes, QR codes, or RFID tags, image recognition systems, or by tracking items ordered from a menu or purchased at a grocery store.

Various embodiments of the disclosed system display a dashboard or other appropriate user interface to a user that is customized based on the user's nutritional needs, such as the user's caloric intake or a set of determined applicable DRI values. The disclosed system calculates an SDIS over a period of time, and displays the score to the user via the dashboard. In these embodiments, the calculated scores are functions of the amount of nutrients and energy over a given time period and are also tailored to an individual user. In such embodiments, the disclosed system calculates nutrient scores by determining whether nutrient content of a consumable is within a range tailored to the user for each nutrient contained in the consumable. The system then composes an average nutrient score based on a personalized set of weighting parameters and/or sensitivity values ascribed to each nutrient that reflect the overall health impact of the consumable for the individual. These numbers are taken as a weighted average of individual nutrient scores, and the weighted average is multiplied by the energy score.

In embodiments of the system disclosed herein, a graphical user interface is provided which advantageously enables, for the first time, users to input data about food consumed in a given period of time and to see an indication of a score, based appropriately on energy consumption, that reflects overall nutritional content of the consume diet. Such graphical user interfaces solve problems not previously solved because they give users access to SDIS data that was heretofore unavailable to track healthiness of a user's diet.

Various embodiments of the disclosed system also provide an advisory functionality. In these embodiments, after calculating an individual's SDIS based on ranges that define that individual's nutrient and caloric needs for a given time period (e.g., a given day), the disclosed system suggests combinations of consumables that can be consumed for the remainder of the time period to result in the individual obtaining the nutrients he or she requires. For example, if an individual indicates that he or she has eaten certain foods for breakfast and lunch, the disclosed system can suggest a dinner menu that will ensure the individual gets all the nutrients he or she needs in the day while still consuming an amount of calories that falls within a caloric intake range applicable to the individual. In this embodiment, the recommendations provided by the disclosed system are optimized; the system determines the impact on the overall SDIS, and suggests foods that result in an optimal increase to the SDIS.

In one embodiment, the system determines the total nutrient content of the consumable or group of consumables before determining a nutrient score for each nutrient. In this embodiment, the nutrient score for each nutrient is less than 1 (or some other maximum) if the nutrient content is outside the range for that individual, and is 1 (or some other maximum) if the nutrient content is in the range for that individual. The amount by which the nutrient score differs from 1 (or some other maximum) indicates the extent to which the nutrient in a consumable is outside the range determined to be ideal for an individual. This scoring calculation also takes into account both the amount by which a nutrient is under-consumed (i.e., is consumed in amount less than a healthy range for the nutrient) and an amount by which the nutrient is over-consumed (i.e., is consumed in an amount greater than the healthy range for the nutrient).

Given the nutrient scores for the individual nutrients of a consumable, the disclosed system further calculates an average nutrient score by computing a weighted average of the scores for the nutrients (with the exception of energy). In various embodiments, this is done by assigning a weighting value to each non-energy nutrient in the scoring profile, multiplying the nutrient score for that nutrient by the weight, and summing the scores of all the scores of the nutrients in the consumables. In an embodiment, the weighting scores sum to 100. As a result, the overall average nutrient score in this embodiment will be a number less than or equal to 100. If the nutrient scores for each nutrient in the consumable are each 1 (meaning that each nutrient of the consumable is within the healthy range for the individual), the overall average nutrient score will be 100 (i.e., the sum of the weights of the nutrient components). Thus, in one embodiment, an average nutrient score of 100 indicates that each of the individual's nutrient requirements are being met, and a number less than 100 indicates they are not, with the difference representing an amount by which the nutrient needs are not being met. In an alternative embodiment, the sum of the scores will equal a number between 0 and 1. This average nutrient score is then multiplied by the energy score to arrive at the SDIS.

It should thus be appreciated that the disclosed system provides the advantage over known systems in that the particular food consumed does not have a single, static score, but rather has a scoring profile or function that is tailored to an individual that can be used to determine scores for the food under different conditions, such as different caloric intake requirements, different amounts of food consumed, or different time periods. The disclosed system is further advantageous in that it accounts for caloric intake in a far more accurate way than any known nutrient scoring systems.

In various embodiments, the disclosed system stores some or all of the values needed to calculate SDIS in one or more databases. For example, the disclosed system may store a table of caloric intake ranges for individuals based on the age, gender, and weight or Body Mass Index (BMI) of the individuals. In this embodiment, to determine an individual's caloric intake range for a given time period, the individual must provide the system with his or her age, gender, and weight or BMI. By performing a database lookup or calculation, the disclosed system can thus determine a caloric intake range for a given time period for a given individual.

In one embodiment, the disclosed system enables a user to customize the SDIS to suit him or her by indicating his or her age, gender, and weight/BMI. This affects the caloric (energy) intake range for the individual, and thus affects the lower and upper healthy range values for each nutrient tracked by the system. In another embodiment, the disclosed system provides for further customization by enabling the user to specify additional information, such as body type, physical activity level, and the like. In this embodiment, the disclosed system uses these additional inputs to adjust not only optimal caloric intake ranges for different individuals, but also lower and upper healthy range values for nutrients tracked by the system. For example, if an individual indicates that he or she is athletic with a relatively high amount of athletic activity, the system may adjust the carbohydrate nutrient range upward to account for the individual's need for additional carbohydrates.

In various embodiments, the disclosed system works in conjunction with a laboratory or other testing facility that generates actual data about individuals using the disclosed system. For example, in one embodiment the disclosed system enables a user to submit a blood spot test or urine test to determine the nutrient composition of the individual's blood, including whether the individual is over- or under-consuming various nutrients. In such embodiments, this testing and labwork enables the system to verify that its recommendations are working—that is, to verify that a user is actually receiving adequate nutrients when the scoring function indicates that his or her intake ranges are within the desired range. In various embodiments, other bodily fluids or samples may be taken (e.g., saliva, stool sample, breath) or tissue samples (e.g. muscle, fat, skin, hair, nail) can be used to perform these verifications.

The invention is claimed as follows:

1. A single dietary intake score determination system comprising:
   a user interface;
   a processor; and
   a memory coupled to the processor, wherein the memory stores instructions which, when executed by the processor, cause the processor to:
   calculate a caloric intake range for a user by multiplying a standard caloric intake range by a calorie multiplier determined, at least in part, by a characteristic of the user;
   display, on the user interface a consumable entry control to enable the user to specify at least one consumable and at least one amount for the at least one consumable;
   determine, via the consumable entry control, amounts of nutrients or energy consumed in the at least one amount for the at least consumable by scanning one or more bar codes, QR codes, or RFID tags, or by tracking one or more items ordered from a menu or purchased at a grocery store;
   calculate an energy score and nutrient scores for each of a plurality of nutrients by determining a value of a piecewise continuous function for each of the plurality of nutrients and energy, wherein the plurality of nutrients comprises at least five nutrients selected from the group consisting of added sugars, calcium, carbohydrates, saturated fat, total fat, folate, fiber, iron, magnesium, potassium, protein, sodium, Vitamin A, Vitamin C, Vitamin D, and Vitamin E, and wherein:
   (a) a nutrient function for each nutrient has a first value for a zero amount of the respective nutrient,
   (b) the nutrient function for each nutrient has increasing values for amounts of the respective nutrient greater than zero and less than a nutrient lower healthy range value, a constant value for amounts of the respective nutrient between the nutrient lower healthy range value and a nutrient upper healthy range value, and decreasing values for amounts of the respective nutrient greater than the nutrient upper healthy range value,
   (c) an energy function for the energy having a first value for a minimum amount of energy, and
   (d) the energy function for the energy having increasing values for amounts of energy greater than the minimum amount and less than an energy lower healthy range value, a constant value for amounts of the energy between the energy lower healthy range value and an energy upper healthy range value, and decreasing values for amounts of energy greater than the energy upper healthy range value, the energy lower healthy range value and the energy upper healthy range value being based on the caloric intake range;
   calculate a single dietary intake score by calculating an average nutrient score based on the nutrient scores for the plurality of nutrients, and by multiplying the average nutrient score by the energy score;
   display, on the user interface a graph representing the single dietary intake score;
   receive a location of the user when the user enters a food purchasing establishment;
   determine, based on the location, a plurality of consumables available to the user in the food purchasing establishment;
   calculate the energy score and the nutrient scores for each of the plurality of nutrients for each of the plurality of consumables;
   calculate a potential single dietary intake score based on the single dietary intake score and the energy score and the nutrient scores for the plurality of consumables; and
   push a notification to the user, in real-time, on the user interface, the notification comprising at least one of the plurality of consumables in the food purchasing establishment that results in an improved or optimized potential single dietary intake score.

2. The single dietary intake score determination system of claim 1, wherein the instructions, when executed by the processor, further cause the processor to display, on the user interface, an activity input control to enable the user to indicate the characteristic of the user.

3. The single dietary intake score determination system of claim 1, which includes an activity monitor, and wherein the instructions, when executed by the processor, further cause the processor to receive data from the activity monitor, the data being indicative of the characteristic of the user.

4. The single dietary intake score determination system of claim 1, wherein the plurality of nutrients used to calculate single dietary intake score include all carbohydrates, proteins, and total fat.

5. The single dietary intake score determination system of claim 1, comprising a plurality of tables of weighting values each specific to a particular population of individuals, and wherein the instructions, when executed by the processor, further cause the processor to determine one of the plurality of tables of weighting values to use to calculate a plurality of single dietary intake scores based, at least in part, on the characteristic of the user.

6. The single dietary intake score determination system of claim 5, wherein the characteristic of the user is one selected from the group consisting of: an activity level of the user, an age of the user, a gender of the user, a weight of the user, a Body Mass Index (BMI) of the user, and a medical condition of the user.

7. The single dietary intake score determination system of claim 1, wherein the instructions, when executed by the processor, further cause the processor to push a second notification to the user, the second notification comprising at least another one of the plurality of consumables in the food purchasing establishment that results in an improved or optimized potential single dietary intake score.

8. The single dietary intake score determination system of claim 7, wherein the instructions, when executed by the processor, further cause the processor to display, on the user interface, at least one control to enable the user to add the at least another one of the plurality of potential consumables to a diet.

9. The single dietary intake score determination system of claim 7, wherein the instructions, when executed by the processor, further cause the processor to display, on the user interface at least one control to enable the user to remove at least a portion of the at least another one of the plurality of potential consumables from a diet.

10. The single dietary intake score determination system of claim 1, wherein the instructions, when executed by the processor, further cause the processor to determine an optimal single dietary intake score for a designated set of consumables, and to display, on the at least one display device, an indication of the optimal single dietary intake score on the graph representing a plurality of single dietary intake scores for a plurality of amounts of the at least one consumable.

11. The single dietary intake score determination system of claim 1, wherein the instructions, when executed by the processor, further cause the processor to calculate the average nutrient score based on the nutrient scores for a set containing fewer than all of the nutrients tracked by the single dietary intake score determination system, the set based on a desired scoring profile for the user.

12. The single dietary intake score determination system of claim 1, comprising a nutrient subset control configured to enable the user to indicate a desired subset of nutrients, and wherein the instructions, when executed by the processor, further cause the processor to calculate the average nutrient score based on the nutrient scores for the desired subset of nutrients.

13. A single dietary intake score determination system comprising:
a user interface configured to scan one or more bar codes, QR codes, or RFID tags, or track one or more items ordered from a menu or purchased at a grocery store;
a processor; and
a memory coupled to the processor, wherein the memory stores instructions which, when executed by the processor, cause the processor to:
calculate a nutrient health score for each of a plurality of nutrients by determining a value of a piecewise continuous nutrient health score function, wherein the plurality of nutrients comprises at least five nutrients selected from the group consisting of added sugars, calcium, carbohydrates, saturated fat, total fat, folate, fiber, iron, magnesium, potassium, protein, sodium, Vitamin A, Vitamin C, Vitamin D, and Vitamin E, and wherein for each of the plurality of nutrients:
(a) the piecewise continuous nutrient health score function is specific to the respective nutrient,
(b) the piecewise continuous nutrient health score function for the respective nutrient has a first value for a zero amount of the respective nutrient consumed over time, and
(c) the piecewise continuous nutrient health score function for the respective nutrient has increasing values for amounts of the respective nutrient consumed over time greater than zero and less than a lower healthy range value, a constant value for amounts of the respective nutrient consumed over time between the lower healthy range value and an upper healthy range value, and decreasing values for amounts of the respective nutrient consumed over time greater than the upper healthy range value;
calculate an energy score by determining the value of a piecewise continuous energy score function, wherein for each of the plurality of nutrients:
(a) the piecewise continuous energy score function has a first value for a minimum amount of energy consumed over time, and
(b) the piecewise continuous energy score function has increasing values for amounts of energy consumed over time greater than the minimum amount and less than a lower healthy range value, a constant value for amounts of energy consumed over time between the lower healthy range value and an upper healthy range value, and decreasing values for amounts of energy consumed over time greater than the upper healthy range value;
calculate a single dietary intake score based on multiplying the energy score and an average nutrient score, wherein the average nutrient score is based on the nutrient scores for the plurality of nutrients and at least one weighting value; and
determine a set of consumables that contain:
(1) an amount of calories within a specified caloric intake range, and
(2) amounts of nutrients for which the nutrient score is optimal for the amount of calories within the specified caloric intake range;
display, on the user interface, a control to enable the user to remove at least one of the consumables from the set of consumables;
receive a location of the user when the user enters a food purchasing establishment;
determine, based on the location, a plurality of consumables available to the user in the food purchasing establishment;
calculate the energy score and the nutrient scores for each of the plurality of nutrients for each of the plurality of consumables;
calculate a potential single dietary intake score based on the single dietary intake score and the energy score and the nutrient scores for the plurality of consumables; and
push a notification to the user, in real-time, on the user interface, the notification comprising at least one of the plurality of consumables in the food purchasing establishment that results in an improved or optimized potential single dietary intake score.

14. The single dietary intake score determination system of claim 13, wherein for each of the plurality of nutrients, the piecewise continuous nutrient score function for the respective nutrient has decreasing values less than the first value for amounts of the respective nutrient consumed over time exceeding a zero-crossing amount, the zero-crossing amount calculable from a sensitivity value for the respective nutrient.

15. The single dietary intake score determination system of claim 14, comprising at least one data storage device configured to store at least one table containing a plurality of weighting value and/or sensitivity value pairs for each of plurality of nutrients.

16. The single dietary intake score determination system of claim 15, wherein one of the weighting value and/or sensitivity value pairs is selected for each of the plurality of nutrients based on a characteristic of the user.

17. The single dietary intake score determination system of claim 16, wherein the characteristic of the user includes at least one selected from the group consisting of:
an age, a gender, a height, a weight, a Body Mass Index (BMI), and an activity level.

18. The single dietary intake score determination system of claim 12, wherein the instructions, when executed by the processor, further cause the processor to calculate scores for consumption over an amount of time.

19. A method of treating nutrient deficiency, overweight or obesity, the method comprising:
calculating a caloric intake range for a user by multiplying a standard caloric intake range by a calorie multiplier determined, at least in part, by a characteristic of the user, the user has one or more of a nutrient deficiency, overweight or obesity;
displaying, on a user interface a consumable entry control to enable the user to specify at least one consumable and at least one amount for the at least one consumable;
determining, via the consumable entry control, amounts of nutrients or energy consumed in the at least one amount for the at least consumable by scanning one or more bar codes, QR codes, or RFID tags, or by tracking one or more items ordered from a menu or purchased at a grocery store;
calculating an energy score and nutrient scores for each of a plurality of nutrients by determining a value of a piecewise continuous function for each of the plurality of nutrients and energy, wherein the plurality of nutrients comprises at least five nutrients selected from the group consisting of added sugars, calcium, carbohydrates, saturated fat, total fat, folate, fiber, iron, magnesium, potassium, protein, sodium, Vitamin A, Vitamin C, Vitamin D, and Vitamin E, and wherein:
(a) a nutrient function for each nutrient has a first value for a zero amount of the respective nutrient,
(b) the nutrient function for each nutrient has increasing values for amounts of the respective nutrient greater than zero and less than a nutrient lower healthy range value, a constant value for amounts of the respective nutrient between the nutrient lower healthy range value and a nutrient upper healthy range value, and decreasing values for amounts of the respective nutrient greater than the nutrient upper healthy range value,
(c) an energy function for the energy having a first value for a minimum amount of energy, and
(d) the energy function for the energy having increasing values for amounts of energy greater than the minimum amount and less than an energy lower healthy range value, a constant value for amounts of the energy between the energy lower healthy range value and an energy upper healthy range value, and decreasing values for amounts of energy greater than the energy upper healthy range value, the energy lower healthy range value and the energy upper healthy range value being based on the caloric intake range;
calculating a single dietary intake score by calculating an average nutrient score based on the nutrient scores for the plurality of nutrients, and by multiplying the average nutrient score by the energy score;
displaying, on the user interface a graph representing the single dietary intake score;
receiving a location of the user when the user enters a food purchasing establishment;
determining, based on the location, a plurality of consumables available to the user in the food purchasing establishment;
calculating the energy score and the nutrient scores for each of the plurality of nutrients for each of the plurality of consumables;
calculating a potential single dietary intake score based on the single dietary intake score and the energy score and the nutrient scores for the plurality of consumables; and
pushing a notification to the user, in real-time, on the user interface, the notification comprising at least one of the plurality of consumables in the food purchasing establishment that results in an improved or optimized potential single dietary intake score; and
the user consuming the at least one of the plurality of consumables in the food purchasing establishment, which results in the improved or optimized potential single dietary intake score.

* * * * *